(12) United States Patent
Mariampillai et al.

(10) Patent No.: US 11,754,267 B2
(45) Date of Patent: Sep. 12, 2023

(54) OPTICAL ALIGNMENT SYSTEM

(71) Applicant: 7D SURGICAL INC., Toronto (CA)

(72) Inventors: Adrian Mariampillai, Toronto (CA); Peter Siegler, Toronto (CA); Jean-Francois Paul, Ste-Catherine (CA); Michael Leung, Markham (CA); Beau Anthony Standish, Toronto (CA); Victor X. D. Yang, North York (CA)

(73) Assignee: 7D SURGICAL INC., Toronto (CA)

( * ) Notice: Subject to any disclaimer, the term of this patent is extended or adjusted under 35 U.S.C. 154(b) by 873 days.

(21) Appl. No.: 15/370,005

(22) Filed: Dec. 6, 2016

(65) Prior Publication Data

US 2017/0167702 A1  Jun. 15, 2017

Related U.S. Application Data

(60) Provisional application No. 62/265,825, filed on Dec. 10, 2015.

(51) Int. Cl.
*A61B 90/35* (2016.01)
*F21V 21/28* (2006.01)
*F21S 8/08* (2006.01)
*F21V 21/108* (2006.01)
*F21V 9/14* (2006.01)
*F21S 6/00* (2006.01)
*H04N 13/254* (2018.01)
(Continued)

(52) U.S. Cl.
CPC .............. *F21V 21/28* (2013.01); *A61B 90/35* (2016.02); *F21S 8/08* (2013.01); *F21V 9/14* (2013.01); *F21V 21/108* (2013.01); *F21S 6/004* (2013.01); *H04N 13/239* (2018.05); *H04N 13/254* (2018.05); *H04N 13/271* (2018.05)

(58) Field of Classification Search
CPC .......... F21V 21/28; F21V 21/108; F21V 9/14; F21S 8/08; H04N 13/02; H04N 5/2254; H04N 5/2256; A61B 90/35
See application file for complete search history.

(56) References Cited

U.S. PATENT DOCUMENTS

| | | | |
|---|---|---|---|
| 4,722,502 A * | 2/1988 | Mueller | F16M 11/10 188/70 R |
| 4,963,903 A | 10/1990 | Cane | |
| 6,132,062 A | 10/2000 | Borders et al. | |

(Continued)

*Primary Examiner* — Shawn S An
(74) *Attorney, Agent, or Firm* — HILL & SCHUMACHER

(57) ABSTRACT

Alignment systems and devices are provided for controlling the alignment of an optical payload. In some embodiments, an optical positioning system is provided that includes a yoke supporting an optical payload. The yoke, which includes a plurality of articulated segments and associated pivot joints, is mechanically coupled to the optical payload, such that when the optical payload is oriented in a given direction, such as towards a distal target, the optical payload is rotatable about a distal pivot axis associated with a distal pivot joint of the yoke. The pivot joints of the yoke may be configured such that the rotation axis associated with a given pivot joint passes sufficiently close to a respective center of mass of a distalward portion of the optical alignment system beyond the given pivot joint, such that the position and orientation of the optical payload is maintained in the absence of external forces.

20 Claims, 21 Drawing Sheets

(51) Int. Cl.
*H04N 13/271* (2018.01)
*H04N 13/239* (2018.01)

(56) References Cited

U.S. PATENT DOCUMENTS

| | | | | |
|---|---|---|---|---|
| 2002/0067426 | A1* | 6/2002 | Nagata | H04N 5/2254 |
| | | | | 348/373 |
| 2002/0113890 | A1* | 8/2002 | Liang | H04N 3/1575 |
| | | | | 348/373 |
| 2004/0179847 | A1* | 9/2004 | Johnson | H04B 10/118 |
| | | | | 398/122 |
| 2009/0318770 | A1* | 12/2009 | Marka | A61B 90/30 |
| | | | | 600/249 |
| 2012/0104283 | A1* | 5/2012 | Dirauf | A61N 5/1082 |
| | | | | 250/492.1 |
| 2015/0245692 | A1* | 9/2015 | Ma | A45B 23/00 |
| | | | | 135/20.1 |

* cited by examiner

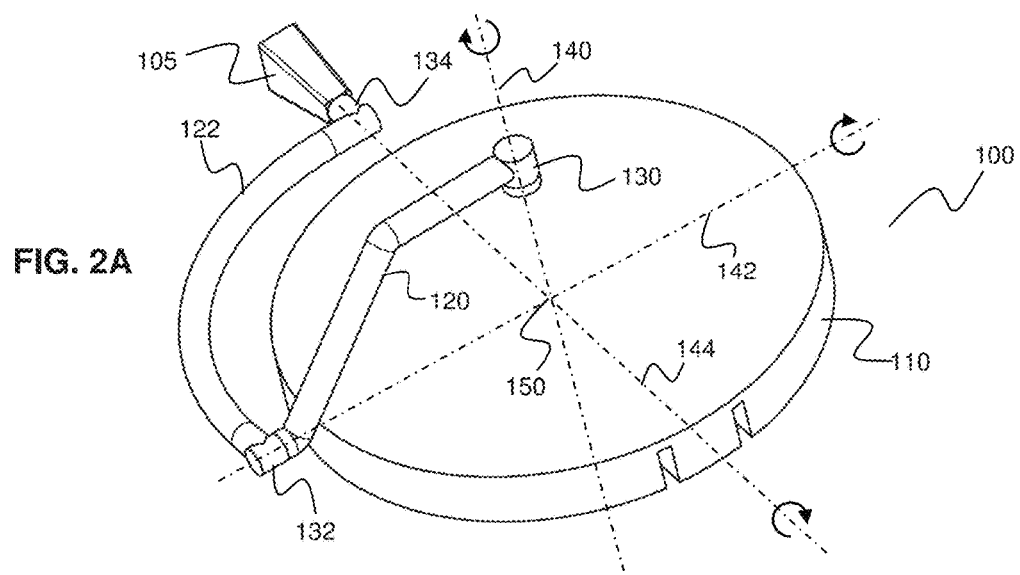
FIG. 2A
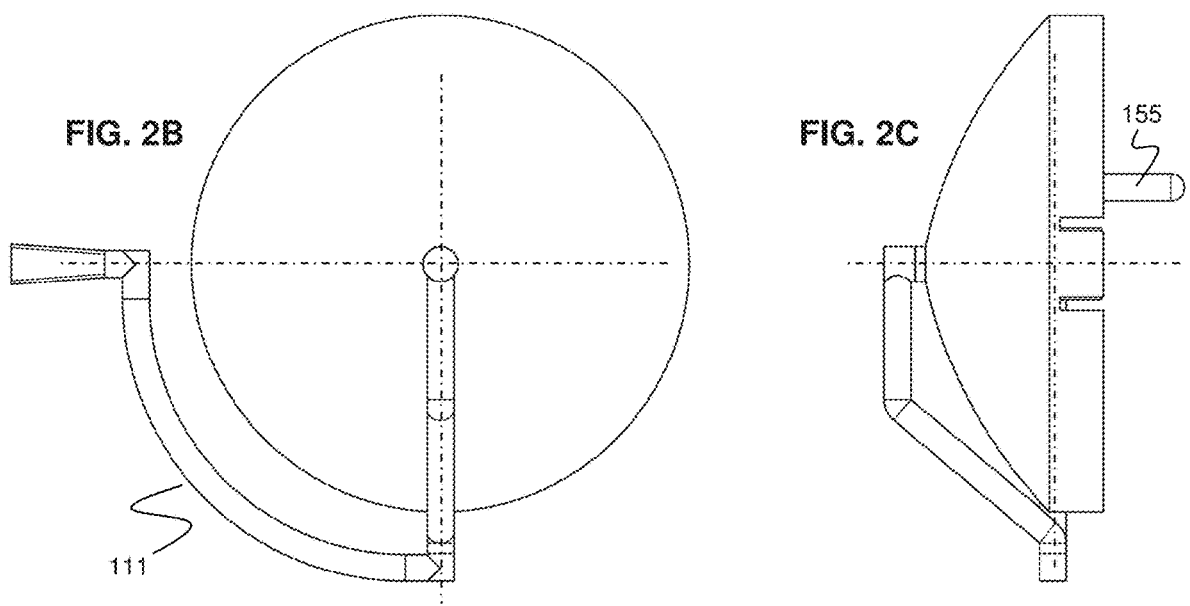
FIG. 2B
FIG. 2C
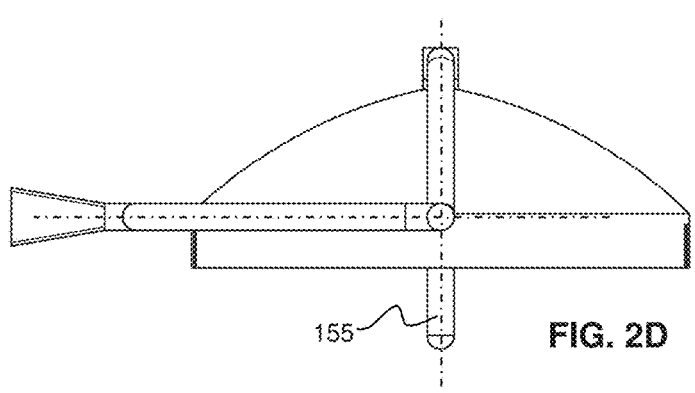
FIG. 2D

OPTICAL ALIGNMENT SYSTEM

CROSS-REFERENCE TO RELATED APPLICATION

This application claims priority to U.S. Provisional Application No. 62/265,825, titled "OPTICAL ALIGNMENT SYSTEM" and filed on Dec. 10, 2015, the entire contents of which is incorporated herein by reference.

BACKGROUND

The present disclosure relates to alignment systems for optical devices. More particularly, the present disclosure relates to systems for the alignment of optical devices employed during medical procedures.

Prior to the advent of electrical surgical lighting systems, operating theatres were built facing south east with large windows to allow natural sunlight to illuminate the surgical field. Electrical surgical lighting systems were first developed in the 1880s and were initially plagued by a number of problems such as thermal emission, instability and high energy consumption. With the advent of light emitting diode (LED) technologies in the 1960's these issues were largely resolved. Today the majority of new surgical lighting systems being developed are based on LED technology. As the technology continues to progress, more advanced features will continue to be integrated into these system. For example, high definition cameras are already commonly found embedded into surgical light heads. A number of yoke designs have been developed to support the positioning of the surgical light head. Today's state of the art yoke designs allow rotation about two orthogonal axis in the plane of light emission. This geometry allows the light head to be directed at virtually any angle. However, as more complex optical systems are integrated into the surgical light head yoke designs with more flexibility will be necessary to support proper positioning of the composite system.

SUMMARY

Alignment systems and devices are provided for controlling the alignment of an optical payload. In some embodiments, an optical positioning system is provided that includes a yoke supporting an optical payload. The yoke, which includes a plurality of articulated segments and associated pivot joints, is mechanically coupled to the optical payload, such that when the optical payload is oriented in a given direction, such as towards a distal target, the optical payload is rotatable about a distal pivot axis associated with a distal pivot joint of the yoke. The pivot joints of the yoke may be configured such that the rotation axis associated with a given pivot joint passes sufficiently close to a respective center of mass of a distalward portion of the optical alignment system beyond the given pivot joint, such that the position and orientation of the optical payload is maintained in the absence of external forces.

Accordingly, in a first aspect, there is provided an optical alignment system comprising:
an optical payload;
a plurality of articulated segments having at least three pivot joints associated therewith, said plurality of articulated segments and pivot joints forming a yoke for controlling the orientation of said optical payload;
wherein said optical payload is mechanically coupled to a distal pivot joint of said pivot joints, such that:

said optical payload is axially directed at a distal target when a distal pivot axis of said distal pivot joint is directed toward the distal target; and
said optical payload is rotatable about the distal pivot axis while remaining axially directed at the distal target;
wherein said at least three pivot joints are configured such that, for any given pivot joint, a respective rotation axis associated therewith passes sufficiently close to a respective center of mass of a respective distalward portion of said optical alignment system beyond said given pivot joint, such that a position and orientation of said optical payload is maintained in the absence of external forces; and
wherein a proximal end of said optical alignment system is connectable to a positioning arm for controlling the position of the optical payload.

In another aspect, there is provided an optical alignment system comprising:
an optical payload, said optical payload having an alignment axis associated therewith, such that said optical payload is aligned with a distal target when the alignment axis is directed toward the distal target
a plurality of articulated segments having at least three pivot joints associated therewith, said plurality of articulated segments and pivot joints forming a yoke for controlling the orientation of the optical payload;
wherein said optical payload is mechanically coupled to a distal pivot joint of said pivot joints such that said optical payload is rotatable about the alignment axis by actuation of the distal pivot joint alone; and
wherein said at least three pivot joints are configured such that, for any given pivot joint, a respective rotation axis associated therewith passes sufficiently close to a respective center of mass of a respective distalward portion of said alignment system beyond said given pivot joint, such that a position and orientation of said optical payload is maintained in the absence of external forces; and
wherein a proximal end of said alignment system is connectable to a positioning arm for controlling the position of the optical payload.

In another aspect, there is provided a optical alignment system for aligning an optical payload relative to a distal target, said optical payload comprising one or more optical components having an optical alignment plane associated therewith, wherein said optical payload is rotatable about a distal axis, the optical alignment system comprising:
a first laser source configured to direct a first laser beam, from a first source location on said optical payload, such that the first laser beam, when unobstructed, passes through a first alignment location, wherein the first alignment location is spatially offset, in a first direction that is perpendicular to the alignment plane, from a point on the distal axis that corresponds to the working distance of said optical payload;
a second laser source configured to direct a second laser beam, from a second source location on said optical payload, such that the second laser beam, when unobstructed, passes through a second alignment location, wherein the second alignment location is spatially offset, in a second direction that is perpendicular to the alignment plane, from the point on the distal axis that corresponds to the working distance of said optical payload, and wherein said first direction is opposite to said second direction, such that the first alignment location and the second alignment location are on opposite sides of the alignment plane; and
a third laser source configured to project a transverse alignment beam within the alignment plane;
wherein the alignment plane is a first alignment plane, and wherein the first source location and the second source location are on opposite sides of a second alignment plane that is perpendicular to the alignment plane and contains the distal axis, such that the first laser beam and the second laser beam are both inwardly directed towards the first alignment location and the second alignment location, respectively;

wherein the transverse alignment beam provides the visual indication of the rotational alignment of said optical payload relative to the distal target; and wherein the first laser beam and the second laser beam produce visible reference marks on the distal target, such that the visible reference marks only intersect the second alignment plane when the distal target is located at the working distance of said optical payload, thereby providing the visual indication of the axial alignment of said optical payload relative to the working distance.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 2A-D show top and side views of an example optical alignment system.

In FIG. 4A, the optical alignment axes of the outer two optical components are inwardly directed, while in FIG. 4B, the optical alignment axes of the outer two optical components are outwardly directed.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Various embodiments of the present disclosure provide alignment systems for aligning an optical payload. Unlike the systems and methods known to those skilled in the art, the example systems and methods disclosed herein enable the alignment of an optical payload such that the optical payload is aligned along, or parallel to, a distal pivot axis of the optical alignment system, thereby permitting subsequent rotation of the optical payload about the distal pivot axis while maintaining directional alignment with a distal target. As described below, the example embodiments disclosed herein may be employed for a wide variety of applications, including surgical illumination, imaging, optical projection, surgical tracking, and navigation.

Figure 1:
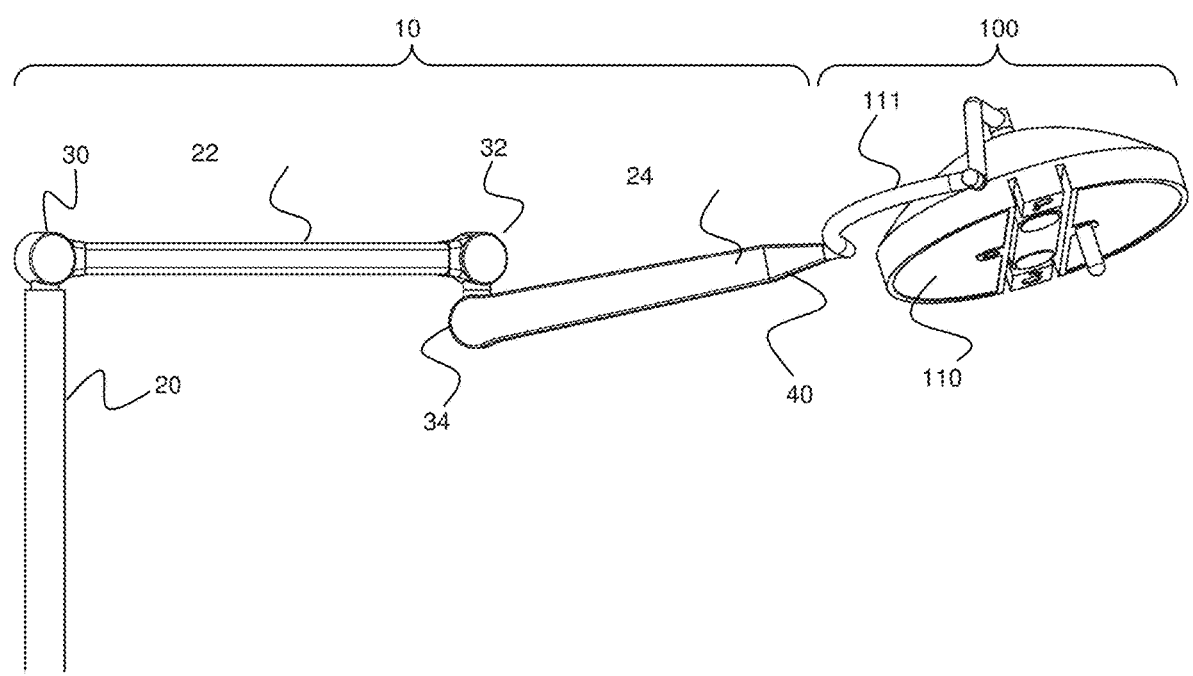
FIG. 1 shows an example optical alignment system for aligning an optical payload with a distal target, where the optical alignment system is shown connected to a three-dimensional positioning arm.

FIG. 1 shows an example embodiment of an optical alignment system 100, including a yoke 111 that supports an optical payload 110, where the yoke 111 is connected to a positioning arm 10. Positioning arm 10 includes a series of articulated segments 20, 22 and 24 that are positionable via rotational joints 30, 32 and 34. The segments may thus be articulated by rotation of the joints in order to control the three-dimensional position of the distal end 40 of the positioning arm. The optical alignment system 100 is connected to the distal end 40 of the positioning arm 10, and is configurable for controlling the orientation and alignment of an optical payload 110. Additionally segment 24 may be a spring arm used to balance the combined weight of the optical alignment system and optical payload 110 located at the distal end 40 of the positioning arm. The spring arm enables the payload's elevation to maintain once positioned without the use of locking mechanisms.

FIGS. 2A-2D show a series of views of an example optical alignment system 100. The optical system includes an optical payload 110 that is mechanically coupled to yoke 111. The optical payload 110 generally consists of a body, frame, or other supporting structure that mechanically supports one or more optical components. Various example configurations of the optical payload 110, and associated optical components, are described in detail below.

The yoke 111 includes a set of articulated segments 120 and 122 having associated pivot joints 130, 132 and 134. As shown in FIG. 2A, a connector 105, or another connection mechanism (e.g. a clamp), may be included to facilitate connection of the yoke 111 to a positioning arm (e.g. the positioning arm 10 of FIG. 1). Alternatively, a connector or connection mechanism may be provided as a component of the positioning arm 10.

Figure 2E:
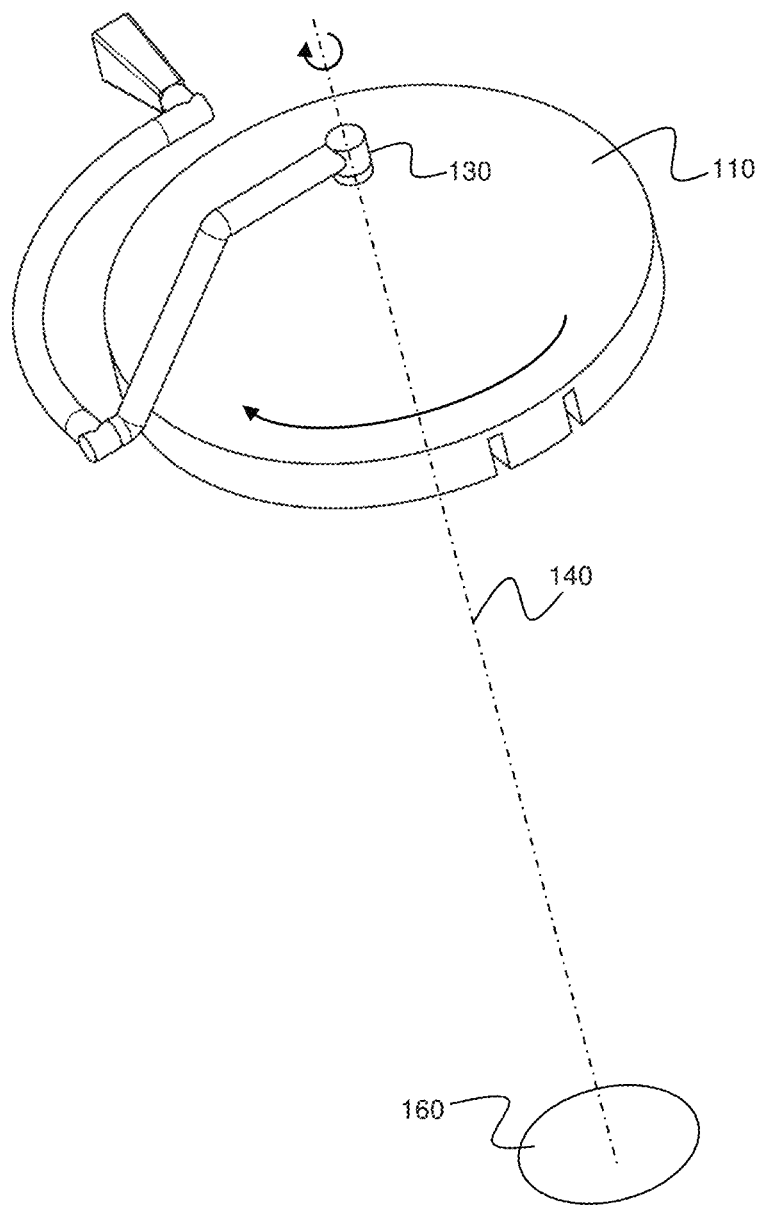
FIG. 2E illustrates how the optical payload, when directed a distal target, may be rotated about the distal pivot axis of the distal pivot joint while continuing to be directed at the distal target.

A first proximal pivot joint 134 is provided for controlling the angular orientation of the optical payload 110 relative to the first pivot axis 144. A first segment 122 mechanically supports the second proximal pivot joint 132 relative to the first proximal pivot joint 134. The second proximal pivot joint 132 is provided for controlling the angular orientation of the optical payload 110 relative to the second pivot axis 142. The first pivot axis 144 and the second pivot axis 142 therefore enable control of the angular orientation of the optical payload 110, such that the first and second proximal joints may be actuated to orient the optical payload 110 in different spatial directions. For example, as shown in FIG. 2E, the first and second proximal joints may be employed to direct the optical payload toward distal target 160.

Although the first pivot axis 144 and the second pivot axis 142 are shown in an orthogonal configuration, it will be understood that in general, these two axes need not be orthogonal, an may be mutually oriented an angle other than 90 degrees.

Referring again to FIG. 2A, a second segment 120 mechanically supports the distal pivot joint 130 relative to the first and second proximal joints 132 and 134. The optical payload 110 is connected to (e.g. mechanically supported by) the distal pivot joint 130, such that the optical payload 110 is rotatable relative to the distal pivot axis 140 of the distal pivot joint 130, and such that the optical payload is axially directed at a distal target when the distal pivot axis 140 is directed at the distal target. This configuration enables the optical payload 110 to be rotated, relative to the distal pivot axis 140, while maintaining alignment of the optical payload with a distal target 160, as shown in FIG. 2E.

The optical payload 110 may be directly connected to the distal pivot joint 130 as shown in the figure, or may be connected thereto via one or more segments or members. For example, an additional segment, coaxial with the distal pivot axis 140, may extend between the distal pivot joint 130 and the optical payload 110.

Referring again to FIG. 2A, the pivot joints of the optical alignment system 100 are configured such that first and second pivot axes, and the distal pivot axis, all mutually intersect at the center of mass 150 of the optical payload 110. Such a configuration of enables the optical payload to be mechanically stable in any orientation under the force of gravity. However, it will be understood that this configuration is merely an example case, and that in other implementations, the axes need not mutually intersect. In practical implementations, each pivot joint will exhibit some frictional resistance to rotation, and the three axes need not intersect the center of mass to achieve a stable configuration of the optical payload 110. In other words, the frictional nature of each pivot joint will permit offsets between the respective axes and the center of mass, while preserving a stable orientation of the optical payload 110.

Figure 2F:
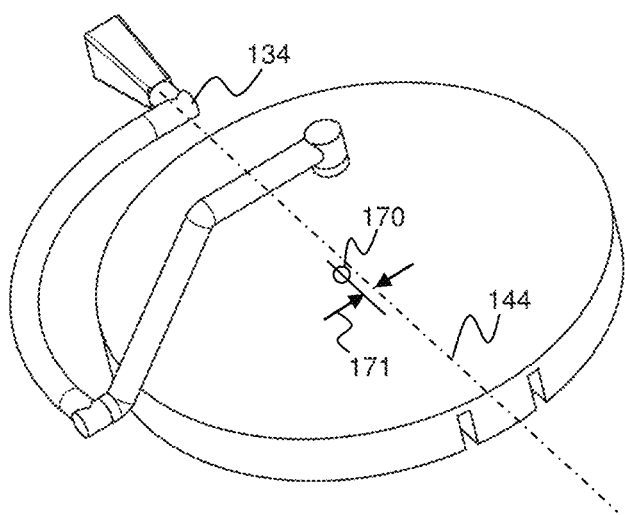
FIGS. 2F-H show how the pivot axes of the optical alignment system are configured relative to the center of mass of the optical alignment system, where the pivot axis of each pivot joint passes sufficiently close to the center of mass of the distalward portion of the optical alignment system (beyond the pivot joint), such that the position and orientation of the optical payload is maintained in the absence of external forces.

For example, FIG. 2F shows an example implementation in which the first pivot axis 144 is spatially offset from the center of mass 170 of the portion of the optical alignment system that is distal to the first proximal pivot joint 134 (i.e. the distalward portion of the optical alignment system). The spatial offset, shown at 171, is sufficiently small that the resulting maximum gravitational torque (when the optical payload is in a horizontal orientation relative to gravity) is less than the static frictional torque of the first proximal pivot joint 134.

Figure 2G:
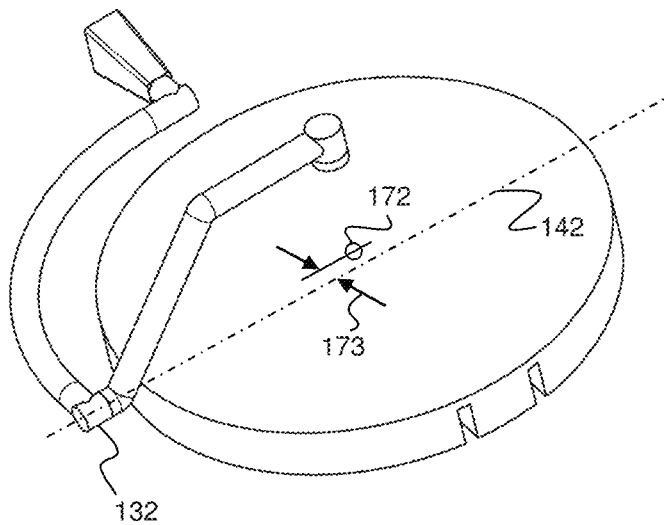

Similarly, as shown in FIG. 2G, the second pivot axis 142 may be spatially offset from the center of mass 172 of the portion of the optical alignment system that is distal to the second proximal pivot joint 132. The spatial offset, shown at 173, is sufficiently small that the resulting maximum gravitational torque (when the optical payload is in a horizontal orientation relative to gravity) is less than the static frictional torque of the second proximal pivot joint 132.

Figure 2H:
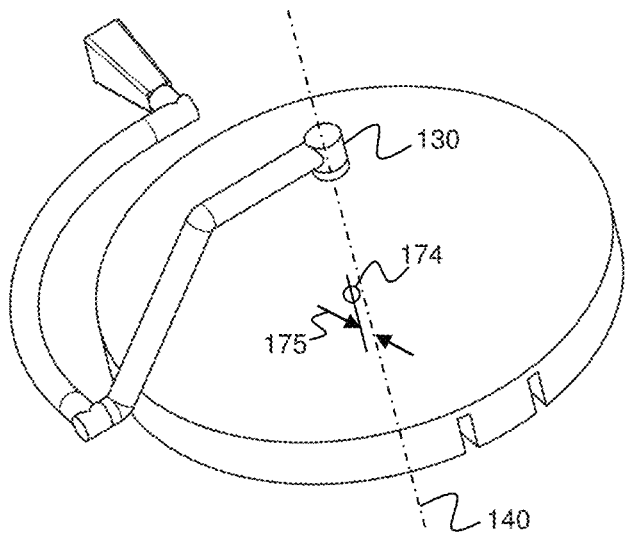

Furthermore, as shown in FIG. 2H, the distal pivot axis 140 may be spatially offset from the center of mass 174 of the portion of the optical alignment system that is distal to the distal pivot joint 130 (e.g. the center of mass of the optical payload, if the optical payload is directly connected to the distal pivot joint 130). The spatial offset, shown at 175, is sufficiently small that the resulting maximum gravitational torque (when the optical payload is in a vertical orientation relative to gravity) is less than the static frictional torque of the distal pivot joint 130.

It will be understood that the maximum spatial offset between the pivot axis of a given pivot joint and the respective distalward center of mass for maintaining a stable orientation of the optical payload 110 will depend on the stiffness of the given pivot joint. The stiffness of each joint may be selected according to the location of the center of mass, and/or the weight, of the optical payload.

In one example embodiment, the stiffness of the joints may be selected so the stiffness of the distal pivot joint 130 is less than the stiffness of the second proximal pivot joint 132, and the stiffness of the second proximal pivot joint 132 is less than the stiffness of the first proximal pivot joint 134. In such an implementation, a force applied to the optical payload 110 (e.g. via handle 155 shown in FIGS. 2C and 2D), in a direction suitable for rotating the optical payload 110 about the distal pivot axis 140, will tend to produce rotation of the optical payload 110 about the distal pivot axis 140 in the absence of rotation about the other pivot axes.

In one example embodiment, the optical alignment system may be configured such that rotation about one or more of the pivot axes is limited by rotational stops. For example, the distal pivot joint 130 may be configured to exhibit rotational stops that limit the rotation of the optical payload 110 over an angular range, such as, for example, within a 90° range, within a 60° range, within a 40° range, within a 20° range, or within a 10° range. These stops can be used to prevent over rotation of the payload and thus over rotation of cables/wires running through the yoke 111 so that they are not damaged. Alternatively, multi-pole slip rings can be used for electronic connections depending on data/signal bandwidth of the payload, in which case no stops are necessary and free rotation of the payload may be allowed.

As described above, and illustrated in FIG. 2E, the first 134 and second 132 proximal joints may be employed to axially direct the optical payload 110 at the distal target 160, and the distal pivot joint 130 may then be employed to control the rotational alignment of the optical payload 110 relative to the distal pivot axis 140, while maintaining directional alignment of the optical payload 110 with the distal target 160. This capability of the optical alignment system may be beneficial for controlling the rotational alignment of two or more optical components of the optical payload 110 relative to the distal target 160.

Figure 3A:
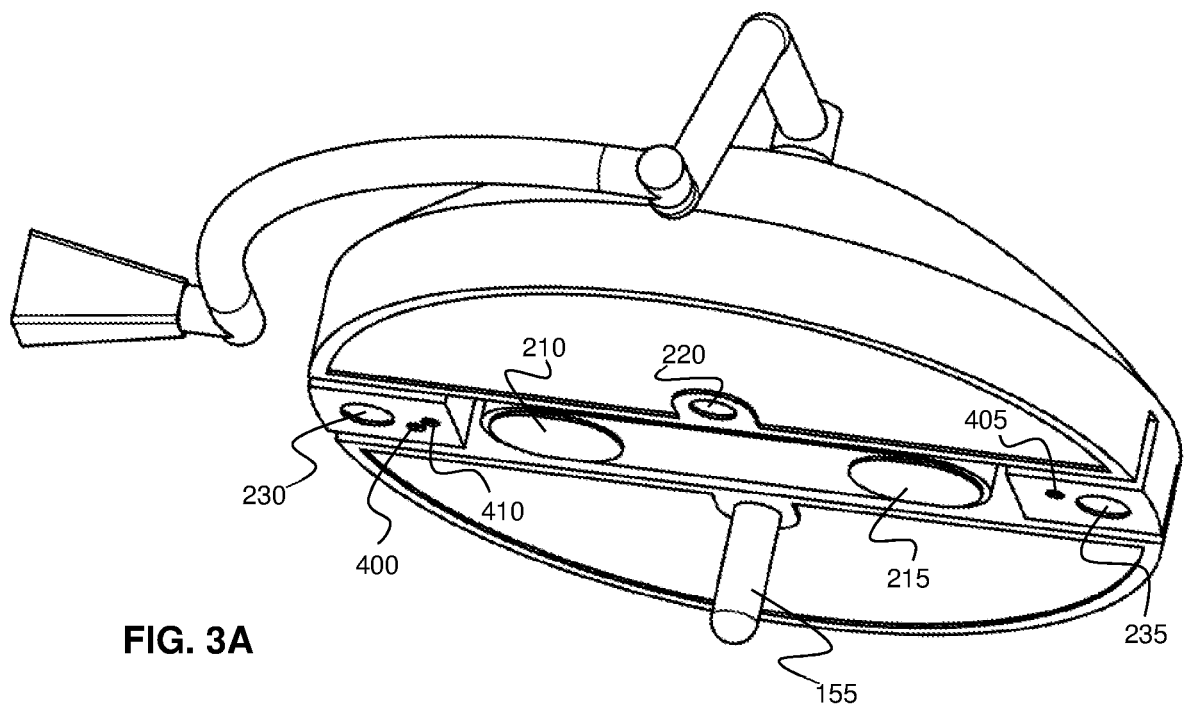
FIGS. 3A-B shows underside views of the example optical alignment system, showing the optical components of the optical payload.
Figure 3B:
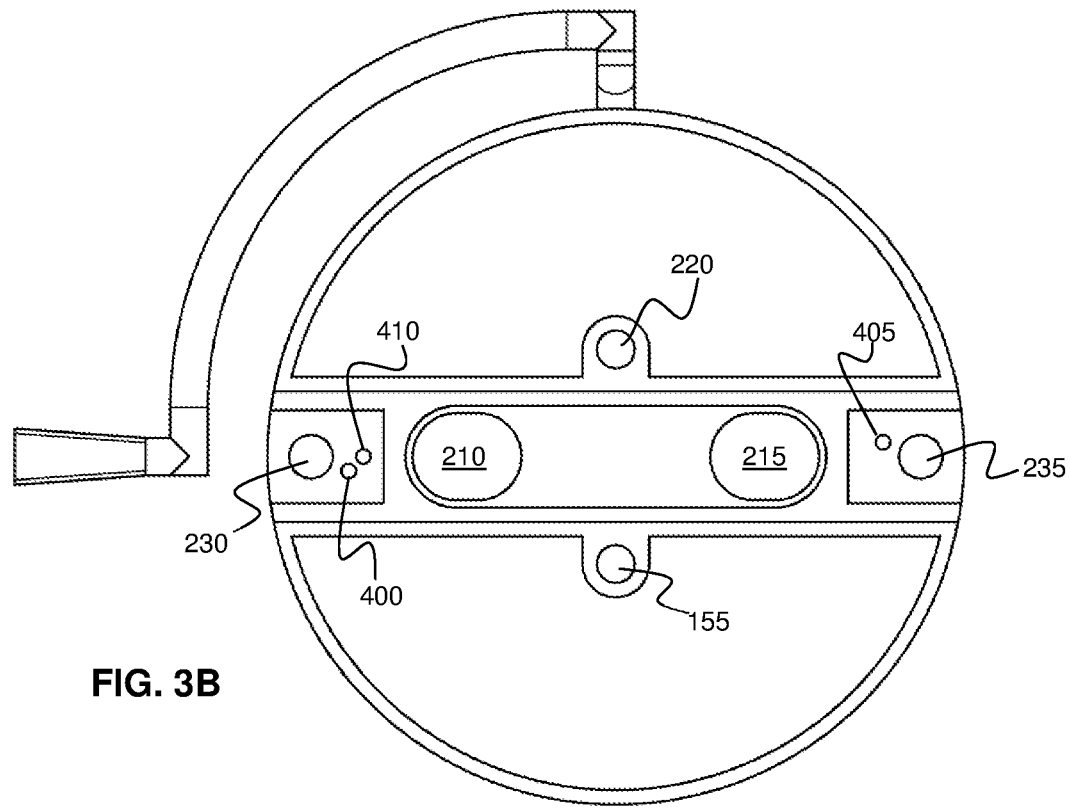
Figure 3C:
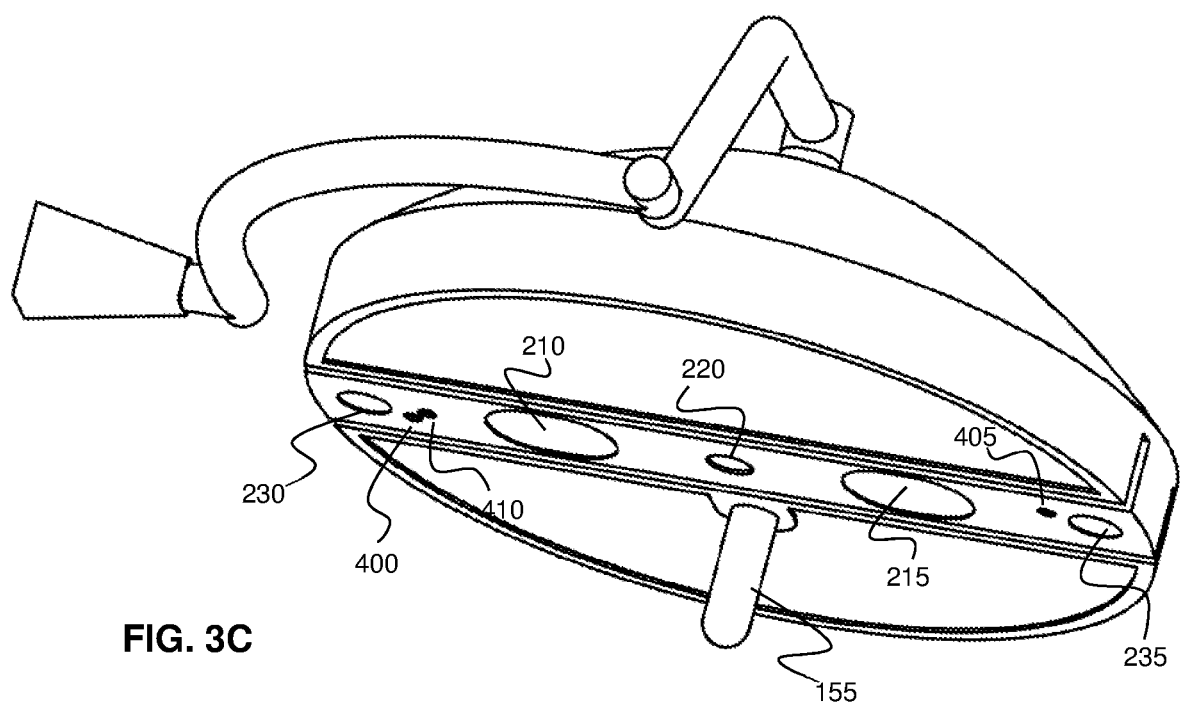
FIGS. 3C-D shows underside views of the example optical alignment system, showing the optical components of the optical payload and centered structured light projection system.
Figure 3D:
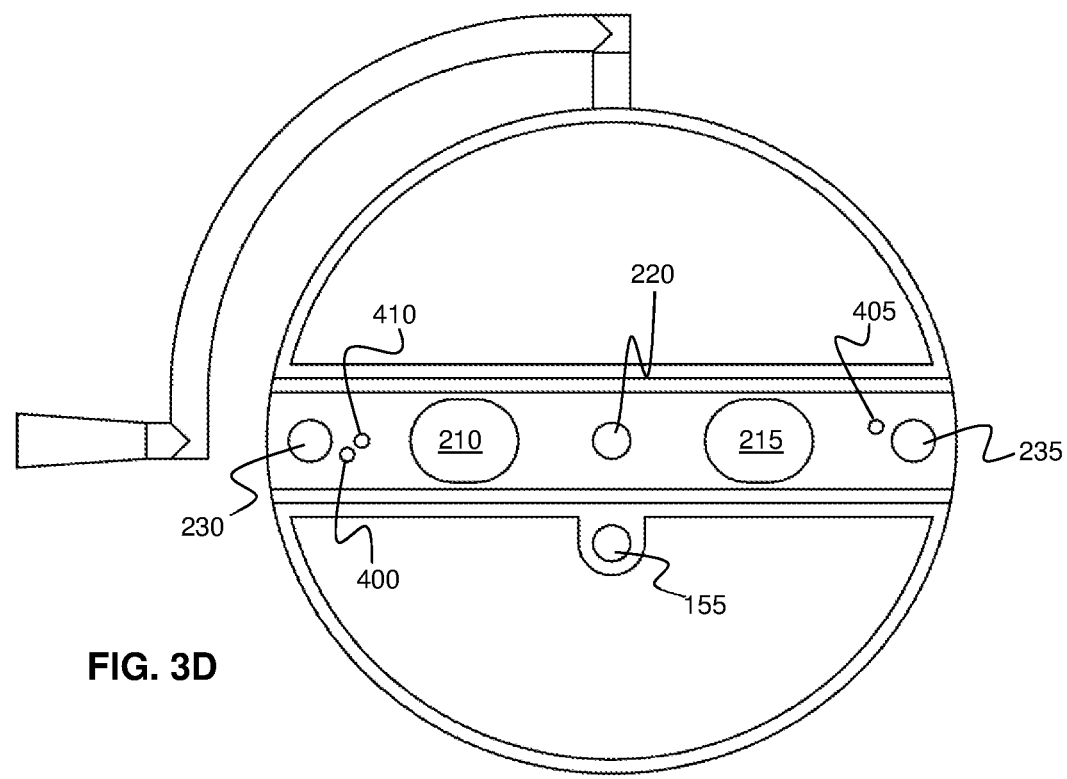

Referring now to FIGS. 3A and 3B, the underside of the example optical payload 110 is shown, illustrating an example configuration of optical components. In the present non-limiting example, the optical payload 110 is a surgical optical payload that includes the following example optical components: a pair of stereoscopic tracking cameras 210 and 215, a structured light projector 220 for projecting structured light patterns onto an object, and a pair of structured light cameras 230 and 235 for imaging the resulting structured light patterns. The example optical payload 110 also includes a handle 155. In order to actuate the rotation about the distal joint it is ergonomically advantageous to place the handle 155 on the distal axis of rotation 140. However, in many situations this may not be possible due to limitations imposed by the optical payload 110 (line of sight or mechanical limitations). In these situations, the handle 155 may be placed as close to the distal axis of rotation 140 as possible. The optical payload 110 may also include a plurality of alignment lasers 400, 405 and 410, which are described in further detail below. Structured light detection systems and stereoscopic tracking systems are described in U.S. Pat. No. 9,119,670, titled "System and Methods for Intraoperative Guidance Feedback", which is incorporated herein by reference in its entirety. FIGS. 3C and 3D show another example configuration in which structured light projector 220 lies on-axis with the cameras 210, 215, 230 and 235.

Figure 4A:
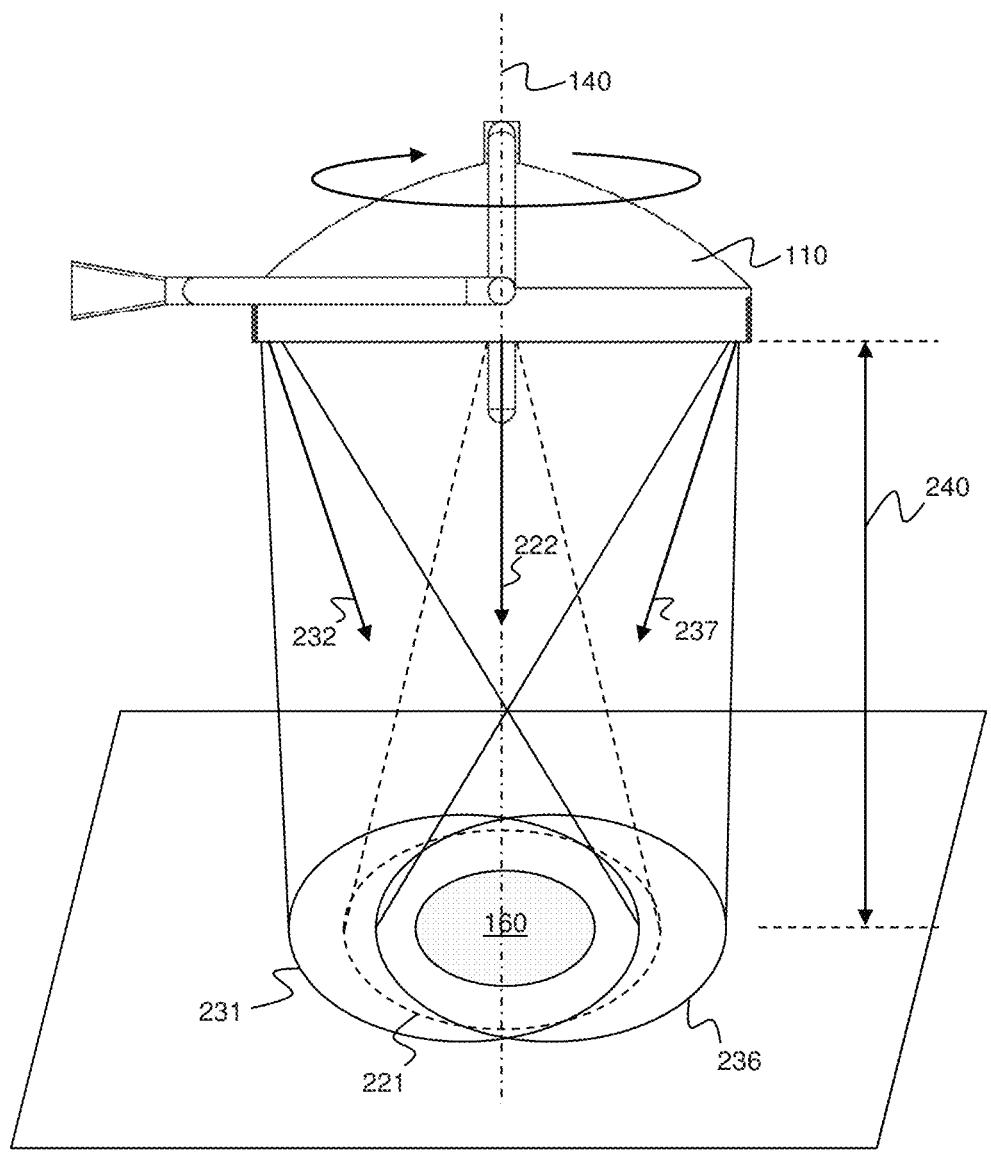
FIG. 4A-B shows how the fields of view of the optical components of the optical payload spatially overlap when the optical payload is directed at a distal target, and how the fields of view maintain their spatial overlap with the distal target when the optical payload is rotated about the distal pivot axis of the distal pivot joint.

FIG. 4A shows how the structured light optical components of the example optical payload 110 are mechanically supported such that their fields of view overlap with the distal target 160. As shown in the figure, the optical alignment system is positioned (e.g. via the positioning arm 100 connected thereto, as shown in FIG. 1) such that the distal target 160 is positioned at a spatial offset 240 that lies within the depth of field of the optical payload 110. The optical payload 110 is also shown oriented such that the distal pivot axis 140 is directed at the distal target 160, whereby the structured light pattern is directed onto the distal target 160 by the structured light projector 220, within its field of view 221. The two structured light cameras 230 and 235 are mechanically supported such that their respective fields of view 231 and 236 each overlap, and also overlap with the field of view 221 of the structured light projector 220, within the depth of field of the optical payload. Accordingly, when the distal pivot axis 140 of the optical alignment system is directed toward the distal target 160, the fields of view 221, 231 and 236 all overlap with the distal target 160.

Figure 4B:
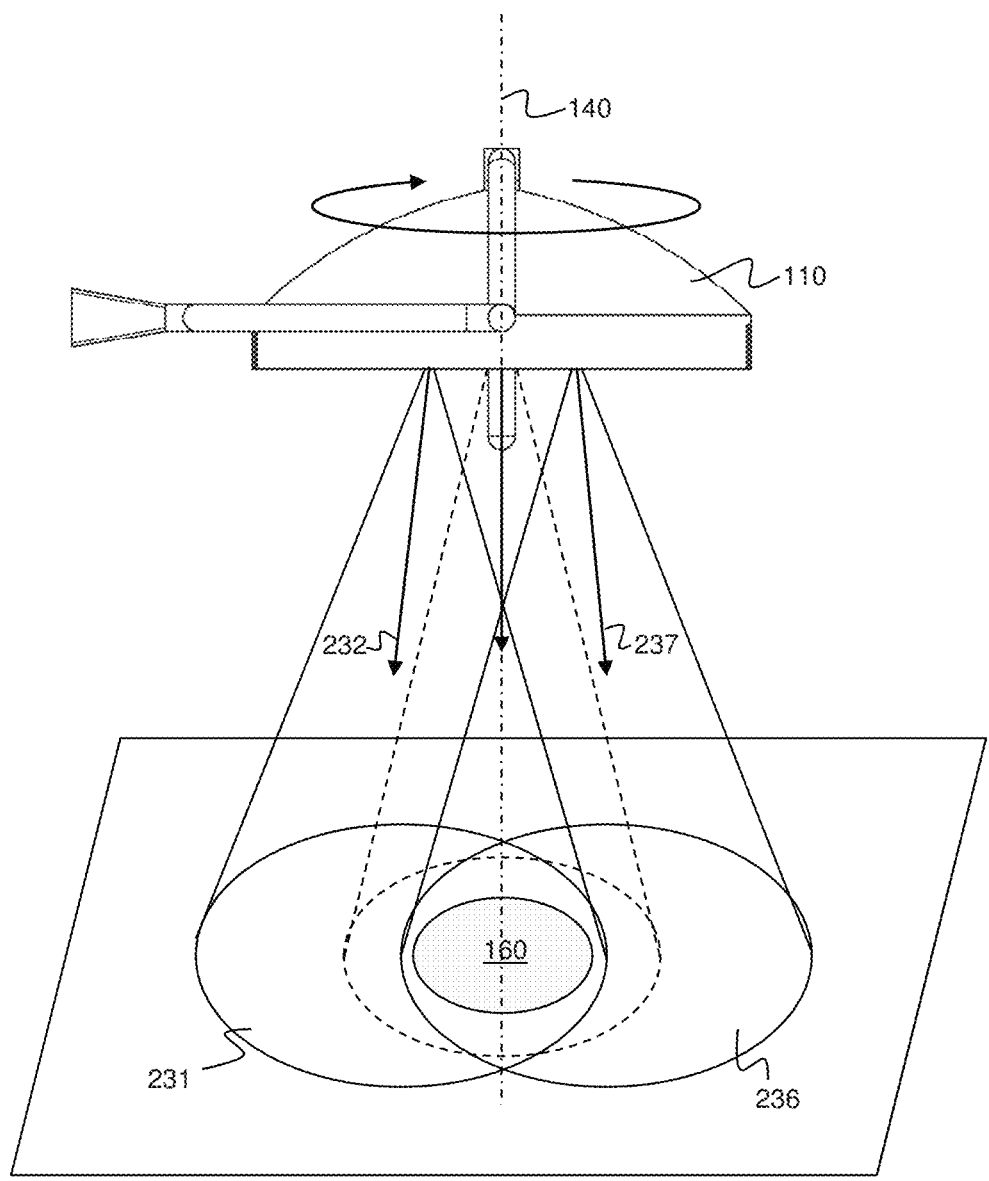

As shown in FIG. 4A, the structured light cameras 230 and 235 are mechanically supporting such that their respective alignment axes 232 and 237 are inwardly directed, and their respective fields of view 231 and 236 are spatially overlapped with the distal target 160. Similarly, the structured light projector 220 is mechanically supported such that its alignment axis 222 is suitably directed for spatially overlapping its field of view 221 with the distal target 160. While the alignment axes 232 and 237 of the structured light cameras 230 and 235 are shown in FIG. 4A as being inwardly directed, FIG. 4B shows an alternative example implementation in which the alignment axes 232 and 237 are outwardly directed, while maintaining suitable spatial overlap of the respective fields of view 231 and 236.

It will be understood that in the example configuration of optical components that is shown in FIGS. 3A and 3B or FIGS. 3C and 3D, in which a pair of tracking cameras are also included, the alignment axes of the tracking cameras will also be suitably aligned in order to achieve sufficient overlap with the distal target 160. It is also noted that although the fields of view are shown as circular, a field of view of any optical component may take on other shapes, such as rectangular.

Figure 4C:
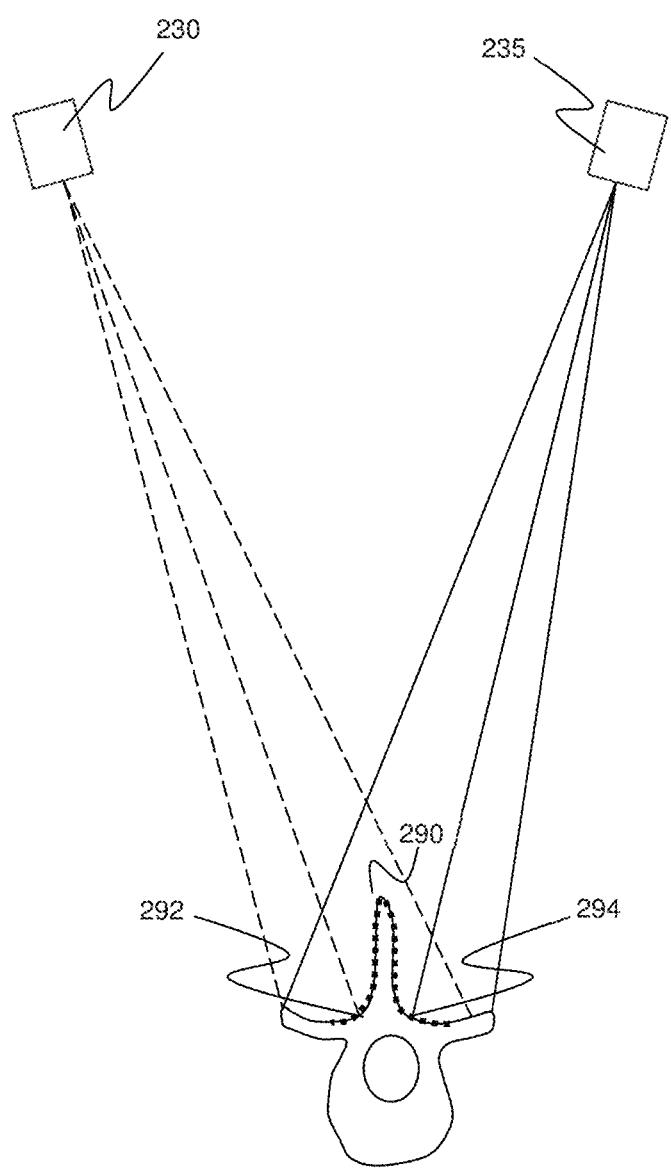
FIGS. 4C and 4D show a comparison of a stereo camera system aligned orthogonally and parallel to the superior-inferior direction of the spine, illustrating the shadowing that occurs in the case of orthogonal alignment.
Figure 4D:
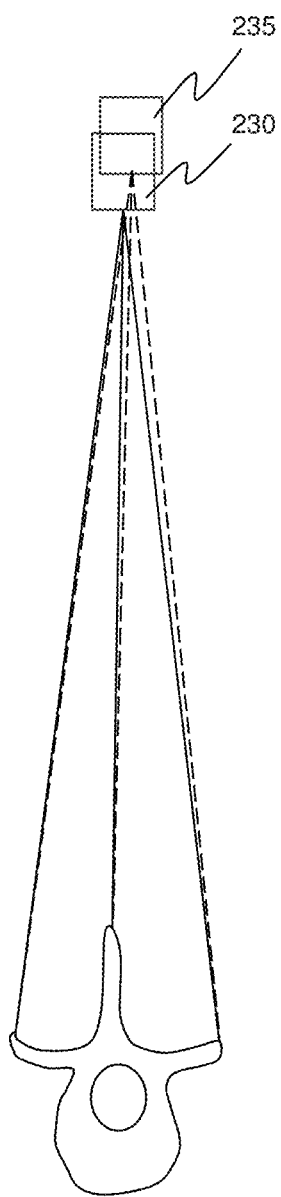

In some applications, the distal target may have a preferential axis or direction, and it may be desirable to align two or more optical components of the optical payload 110 to the preferential axis. In one non-limiting example application, the distal target may be a solid tissue structure of a subject, such as an exposed spinal portion of the vertebral column. When employing structured light to detect a surface profile of an exposed vertebral surface, it may be beneficial to orient the structured light cameras such that the alignment plane between (baseline) the cameras is oriented to the superior-inferior direction of the spine. If the cameras deviate from this orientation the spinous processes create a line of sight obstruction for each of the cameras. Since only regions which are captured by both cameras are reconstructed, this leads to voids in the point cloud on the laminar surfaces. To further illustrate this FIGS. 4C and 4D show the two different configurations, one in which the camera baseline is orthogonal to the superior-inferior direction of the spine and one in which the baseline is parallel to the superior-inferior direction of the spine. As shown in FIG. 4C the right camera 235 is obstructed by the spinous process 292, leading to a shadowing effect on the left laminar surface 292. Similarly the left camera 230 is also obstructed by the spinous process 290, leading to a shadowing effect on the right laminar surface 294. Since only surfaces imaged by both cameras can be reconstructed, both laminar surfaces 292 and 294 would not be reconstructed. FIG. 4D shows another configuration in which the left and right cameras 235 and 230 are parallel to the superior-inferior direction of the spine. In this situation the laminar surfaces are captured by both cameras, resulting in a more complete surface being reconstructed.

Figure 5A:
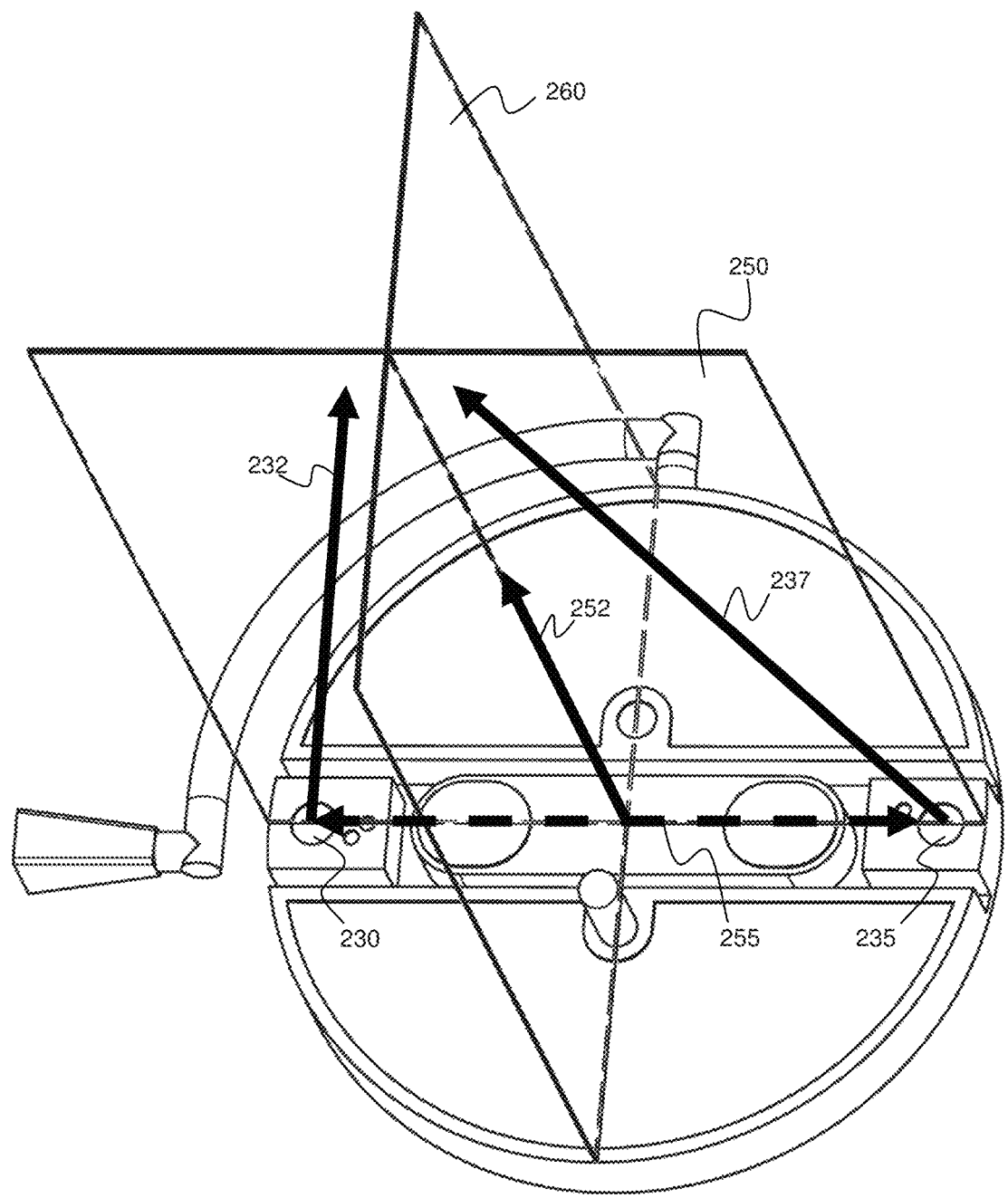
FIG. 5A shows the underside of the optical payload of the example optical alignment system, identifying an alignment plane associated with two of the optical components.

As shown in FIG. 5A, the optical components of the optical payload 110 may be spatially configured and mechanically supported such that the alignment axes of a pair of optical components (i.e. at least two optical components) lie within an alignment plane. In the figure, it can be seen that the respective optical alignment axes 232 and 237 of the structured light cameras 230 and 235 lie within the alignment plane 250 (in the present example embodiment, the alignment axes of the tracking cameras would also lie in this plane). This plane may also, or may alternatively, be defined based on the plane that includes the normal (axial) vector 252 and the baseline 255 extending between and bisecting the two structured light cameras 230 and 235. It is noted that FIG. 5A also shows an additional plane 260 that lies orthogonal to the alignment plane 250.

Figure 5B:
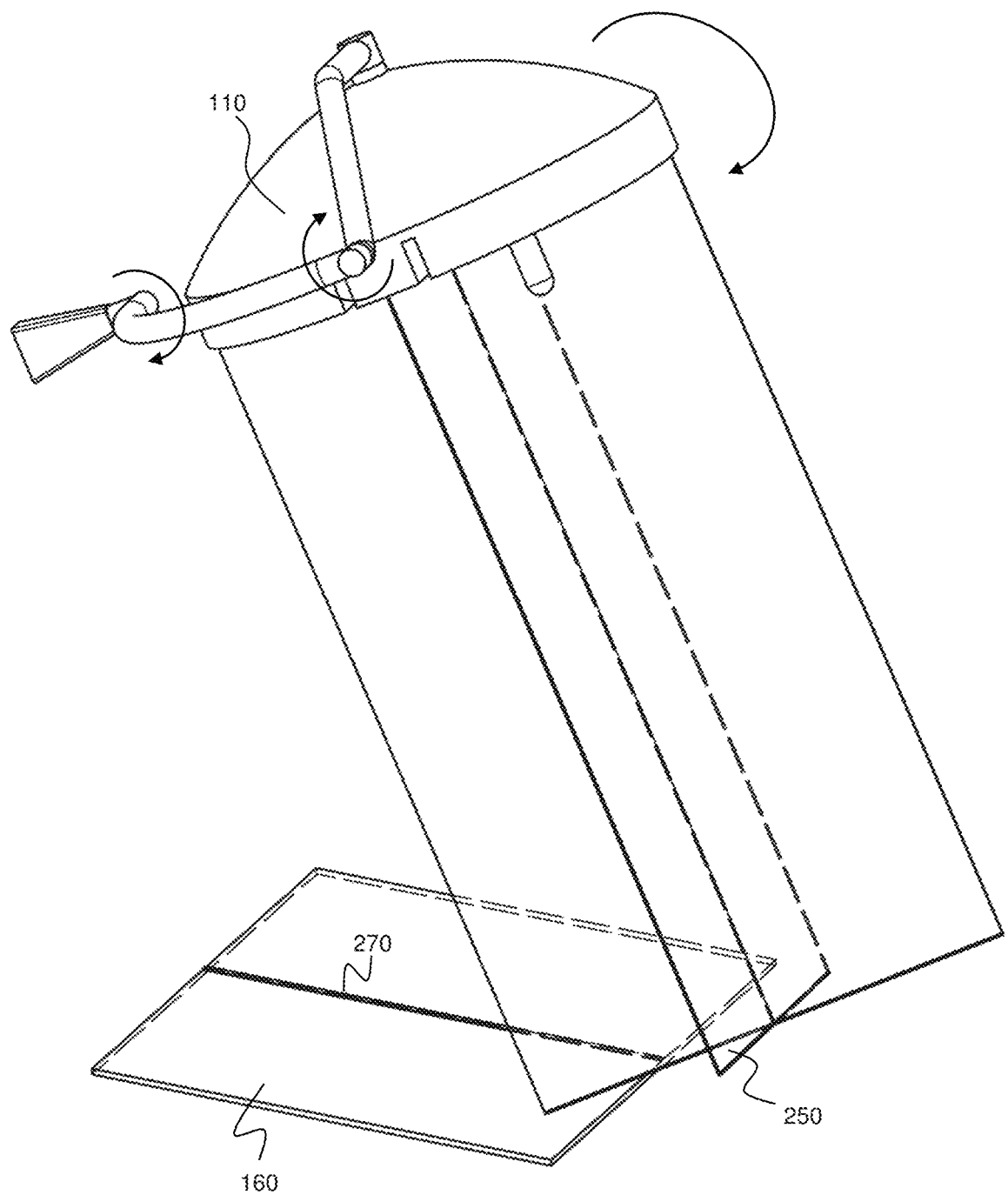
FIGS. 5B-5D illustrate a method of aligning the optical payload with a distal target, where the distal target has a distal target axis (such as the axis of a spine), and where the optical payload is aligned with the distal target such that the alignment plane of the optical components is aligned with the distal target axis.
Figure 5C:
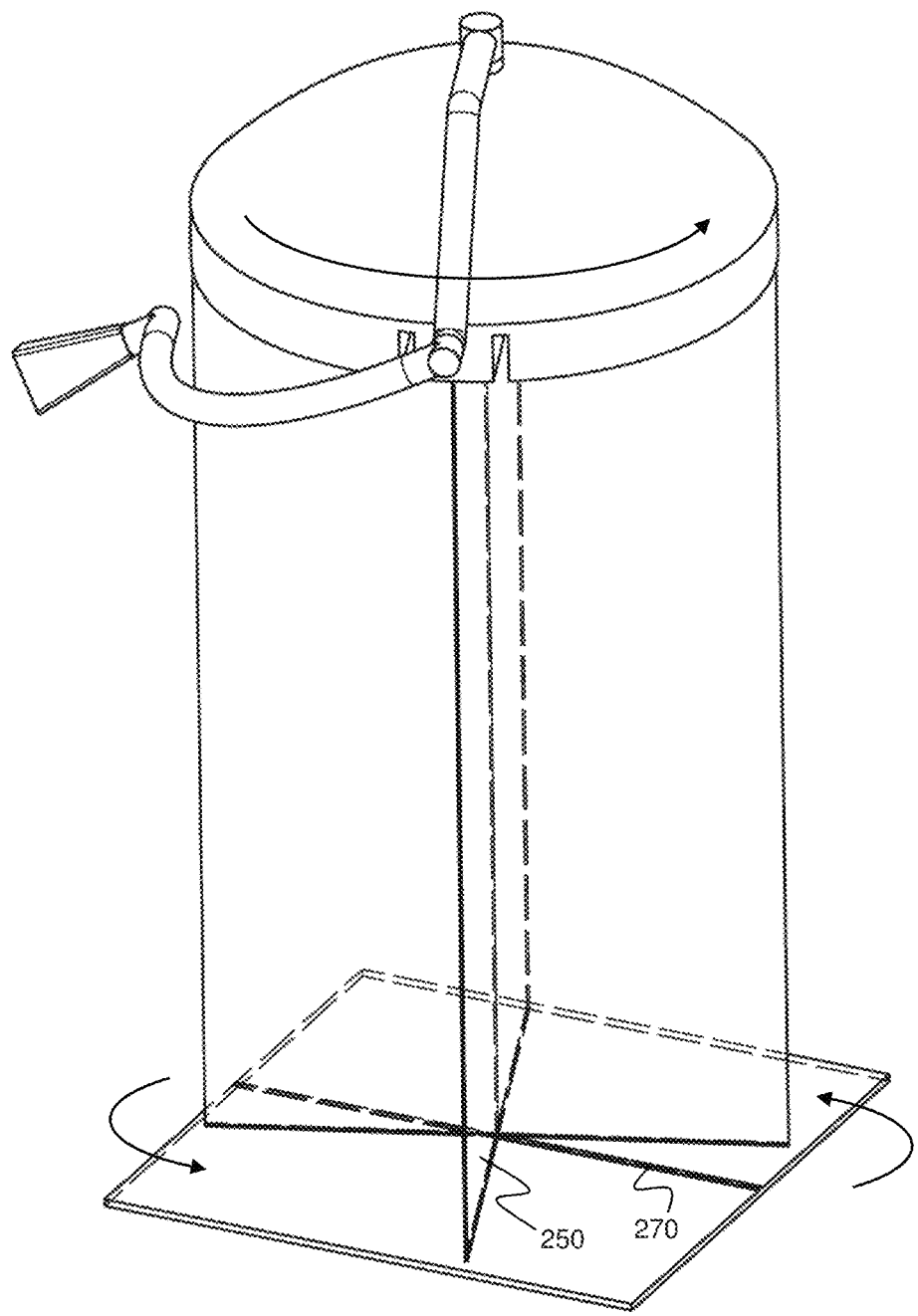
Figure 5D:
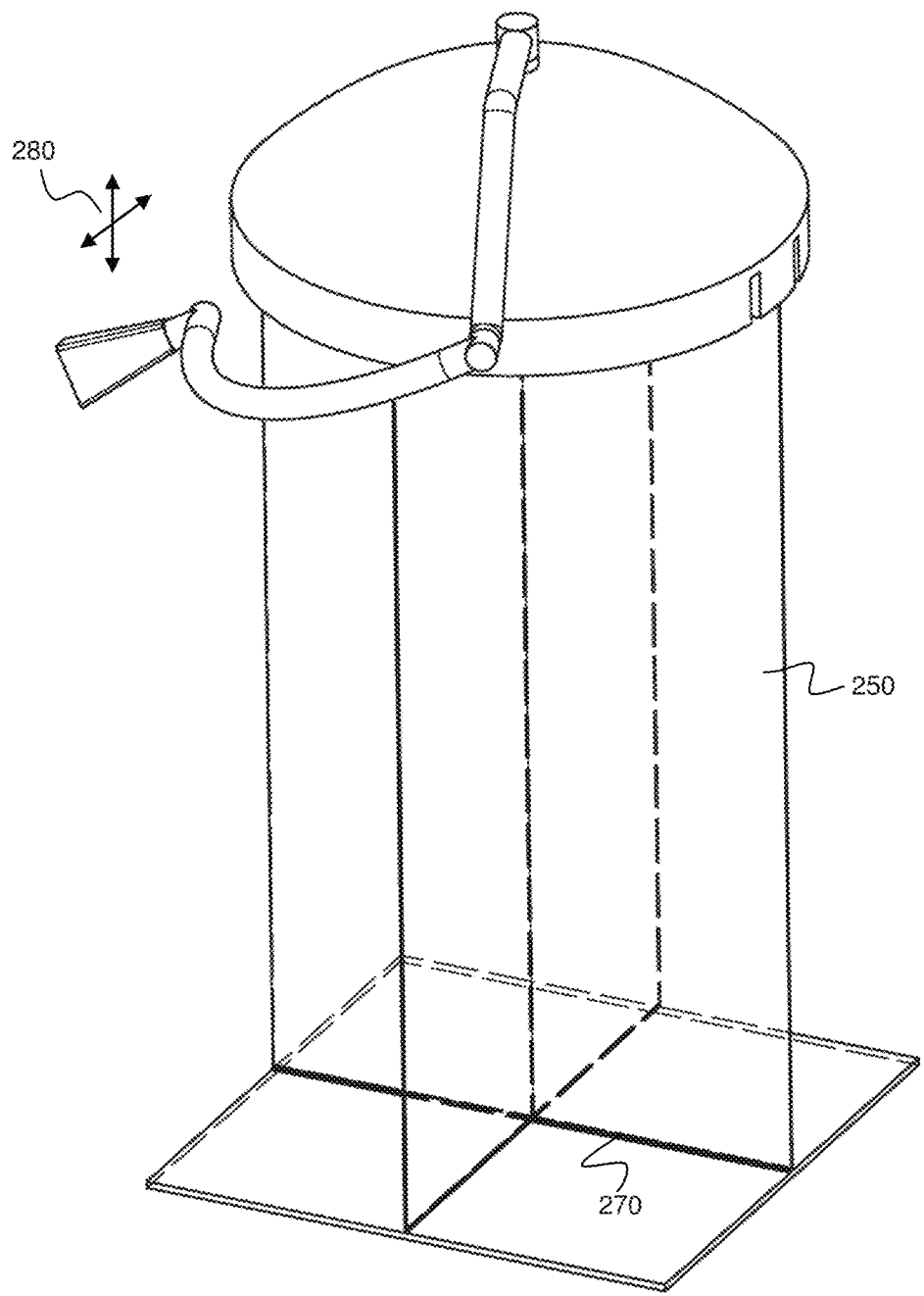
Figure 5E:
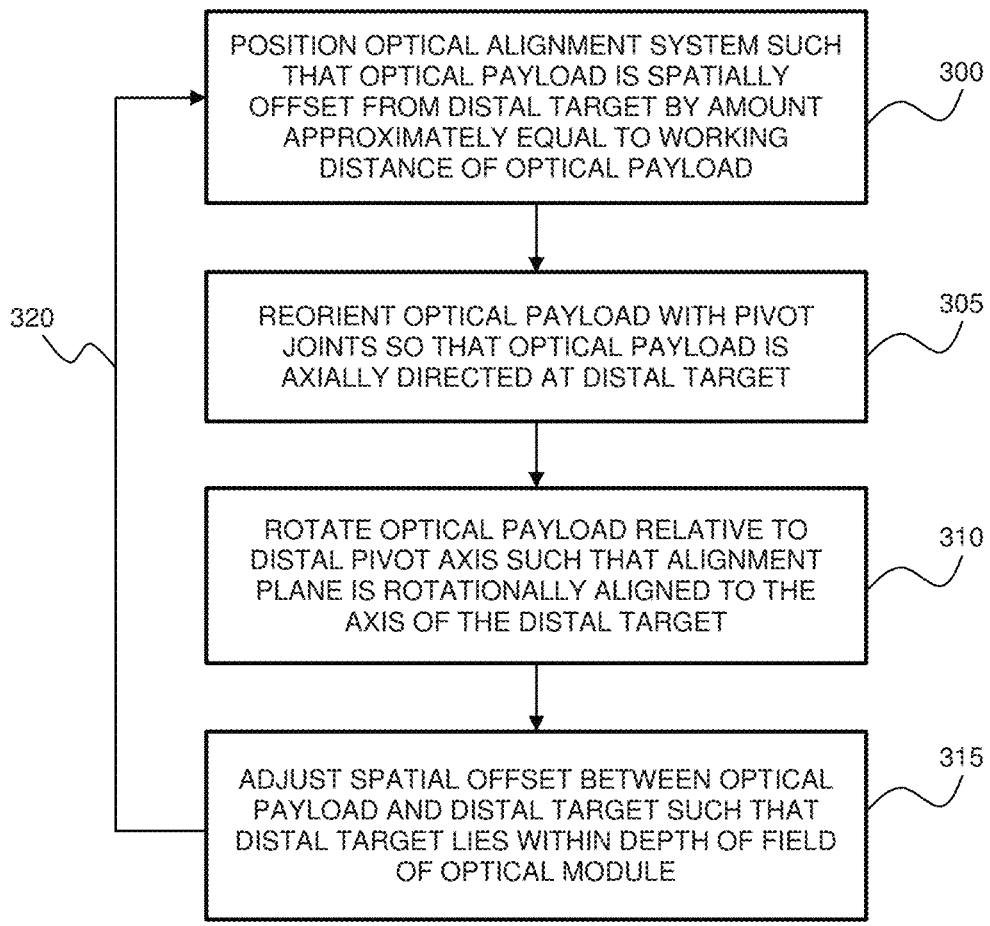
FIG. 5E is a flow chart illustrating an example method of employing the optical alignment system to align the optical payload to a distal target.

FIGS. 5B-5D, and the flow chart shown in FIG. 5E, illustrate the process of aligning the example alignment system relative to a distal target such that the alignment plane 250 overlaps with a distal target axis 270 (for example, the longitudinal direction of the spine). In FIG. 5B, and in step 300 of the flowchart shown in FIG. 5E, the optical alignment system 110 is initially positioned (e.g. using a positioning arm connected to the optical positioning system) such that the optical payload 110 is spatially offset from the distal target by an amount that is approximately equal to the working distance of the optical payload 110. For example, the optical positioning system may be initially positioned such that the difference between the spatial offset and the working distance is a value that lies within the depth of field of the optical payload 110. Alternatively, the initial position may be selected with less accuracy, such that the difference between the spatial offset and the working distance is greater than the depth of field of the optical payload 110. The initial position may be selected such that the difference between the spatial offset and the working distance is less than 5 cm, 10 cm, 20 cm, 25 cm, 50 cm, or another suitable threshold, as determined based on the application.

In step 305 of the flowchart shown in FIG. 5E, the optical payload 110 is reoriented using the optical positioning system, via the first and second proximal pivot joints, as shown by the arrows in FIG. 5B, in order to align the optical payload 110 with the distal target 160, as shown in FIG. 5C.

In step 310, the optical payload is then rotated relative to the distal pivot axis 140, such that the alignment plane 250 is aligned with the distal target axis 270. For example, the optical payload 110 may be rotated as per the arrows shown in FIG. 5C, such that the alignment plane 250 overlaps with the distal target axis 270, as shown in FIG. 5D.

Although the configuration shown in FIG. 5D appears to represent a fully-aligned state, it may be necessary or beneficial to reposition the optical positioning system, without adjusting its orientation, in order to achieve a suitable spatial offset between the optical payload and the distal target. For example, the positioning arm 10 may be employed to raise or lower the optical positioning system such that the spatial offset between the optical payload 110 and the distal target 160 approximately equals the working distance of the optical payload 110, or, for example, such that the distal target 160 lies within the depth of field of the optical payload 110. This additional positioning step, which may optionally be performed (e.g. it may not be necessary if the spatial offset is already sufficiently close to the working distance), is shown at step 315 of the flow chart of FIG. 5E. The additional positioning step may additionally or alternatively be performed in order to correct for any lateral positioning offsets between the alignment plane 250 and the distal target axis 270 (e.g. if the alignment plane is itself spatially offset from the distal pivot axis 140). The vertical and lateral alignment corrections are schematically show by arrows 280 in FIG. 5D. As shown at step 320 of the flow chart, the reorienting and repositioning steps may be performed one or more times in an iterative manner.

Although the preceding example embodiment illustrates an optical payload having an alignment plane that is associated with two or more optical components, it will be understood that an alignment plane (or a preferential axis, or a preferential alignment axis) may be associated with a single optical component. For example, a single optical component may have an alignment axis that is directed at an oblique angle relative to the distal pivot axis, and the alignment plane may include the alignment axis. In another example embodiment, an optical component may have a polarization axis, and the alignment plane may include the polarization axis. The alignment plane may include the distal pivot axis, or be parallel to the distal pivot axis. In another example, an optical component may illuminate the distal target, and/or a region around the distal target, with an optical projection, where it may be important, useful, or beneficial to rotate the optical projection relative to the distal target. For example, images, text, symbols, alignment guides, frames, masks, and/or other information may be optically projected onto and/or around the distal target. The projected images or information may appear rotated about the distal target axis to a user viewing the distal target from an arbitrary location. The user could use the distal pivot axis to rotate the optical projection so that it is easily readable from their arbitrary location.

Figure 6A:
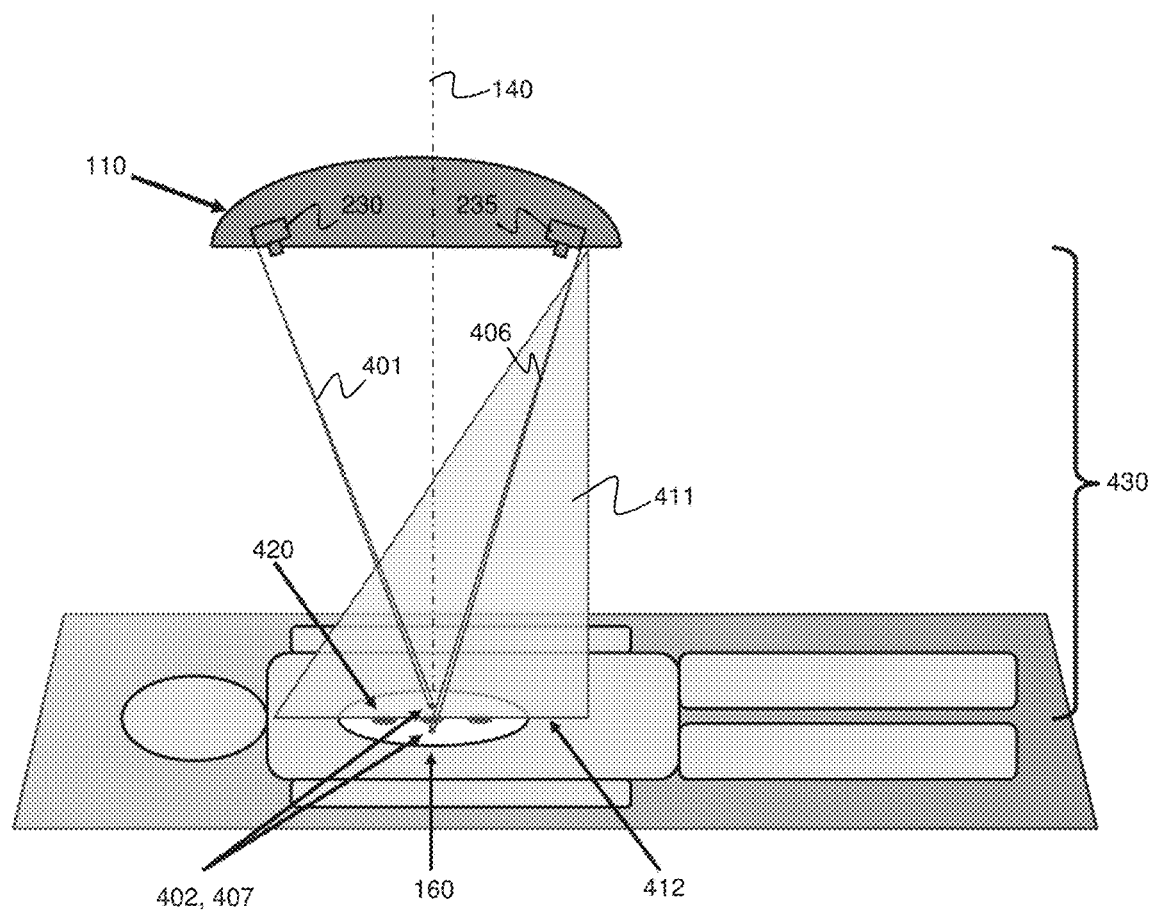
FIG. 6A illustrates an example optical alignment system that includes alignment lasers for rotational alignment and for depth alignment of the optical payload, illustrated for the example application of aligning a structured light optical payload relative to the spine.
Figure 6B:
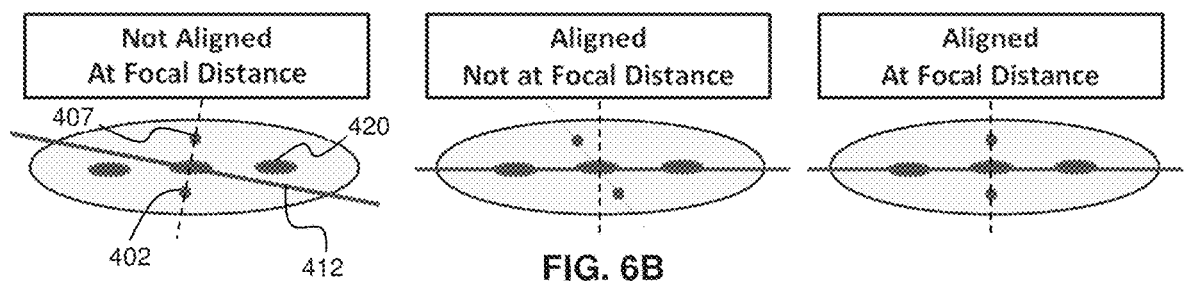
FIG. 6B shows the spatial configuration of the alignment laser projections for three different alignment states for the example optical alignment system shown in FIG. 6A.

Accordingly, in some example embodiments, the optical payload includes one or more optical components, where at least one optical component has an alignment plane associated therewith, and where the at least one optical component is provided such that, when the optical payload is directed at a distal target, the alignment plane is rotatable relative to the distal target by rotating the optical payload about the distal pivot axis, while maintaining axial alignment of the optical payload with the distal target. As noted above, the alignment plane may include, for example, a polarization axis of one or more polarization components, a geometrical axis associated with two or more optical components, such as an axis directed along the baseline separating two optical components, or an alignment axis associated with an optical component, where the alignment plane includes, or is parallel to, the distal pivot axis. In one example embodiment, one or more alignment lasers may be incorporated into (or integrated with) the optical payload 110 in order to provide visual feedback for aligning the optical payload according to the steps illustrated in FIGS. 5B-5E. In one example embodiment illustrated in FIGS. 6A and 6B, the optical payload 110 (which is shown including structured light detection cameras 230 and 235) may include a first laser source that is configured to project a horizontal beam onto the distal target 160 (a surgical cavity in the present example). Such a laser source is shown integrated into the example optical payload 110 of FIGS. 3A and 3B as first laser source 410. The first laser source 410 projects a horizontal beam 411 onto the distal target 160, forming a horizontal stripe 412. The horizontal strip provides a clear visual indication of the present angular orientation of the alignment plane 250 of the structured light cameras 230 and 235 relative to features on the distal target 160, thereby allowing direct visual confirmation of when the optical payload 110 has been properly rotationally aligned about the distal pivot axis 140. For example, as shown in FIG. 6B, the correct alignment of the horizontal stripe 412 with the spinal column 420 is clearly observable in the central and right views, while the left view shows incorrect alignment.

In another example embodiment, a pair of alignment lasers may be employed to direct inwardly-directed laser beams onto the distal target 160, thereby projecting a pair of laser spots onto the distal target 160. Such a pair of alignment lasers are shown in FIGS. 3A and 3B as alignment lasers 400 and 405. The inwardly directed beams from alignment lasers 400 and 405 are shown as beams 401 and 406 in FIG. 6A. These beams are directed on opposite sides of the alignment plane 250, such that laser beams 401 and 406 have a minimal relative spatial offset at an axial distance from the optical payload 110 that corresponds to the working distance of the optical payload 110. The configuration shown in FIG. 6A corresponds to the case in which the distal target 160 is located at the working distance, such that the laser spots 402, 407 produced by corresponding laser beams 401 and 406 have a minimal spatial separation.

Figure 7A:
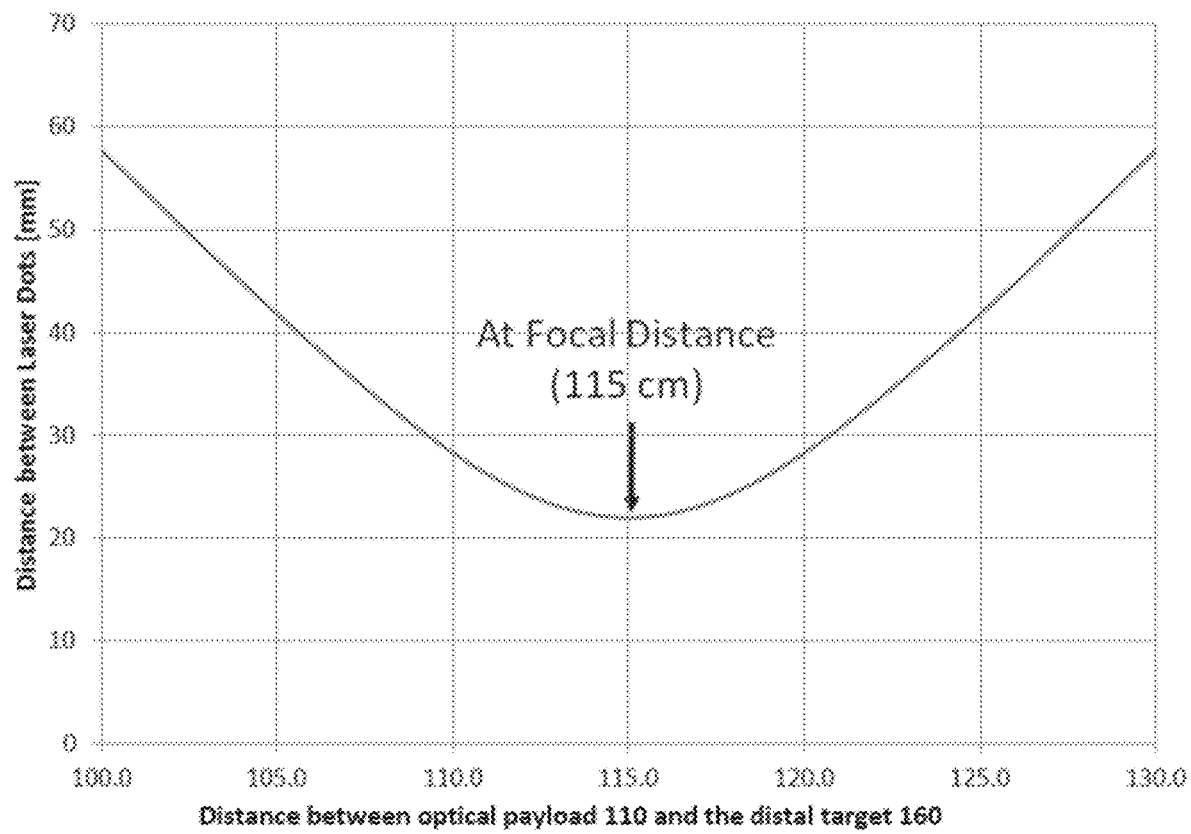
FIG. 7A is a plot showing the relationship between the separation of the laser spots and the spatial offset between the optical payload and the target for an example configuration of the optical system shown in FIG. 6A.
Figure 7B:
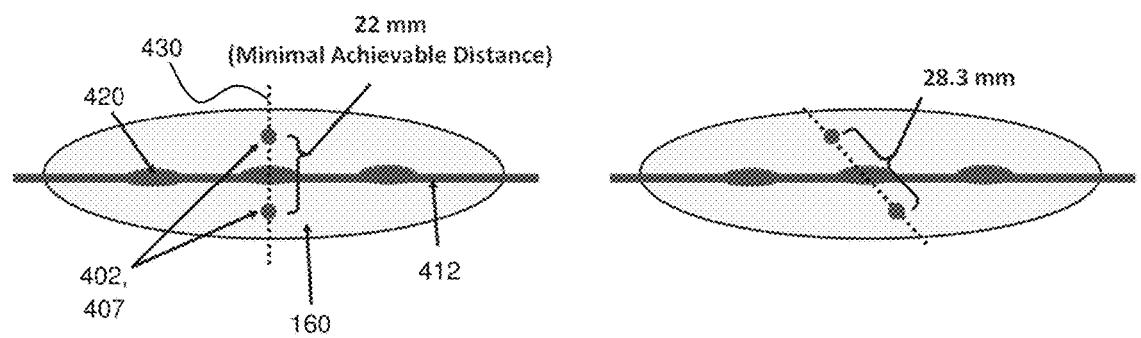
FIG. 7B is shows the spatial configuration of the alignment laser projections for two different alignment states of the example optical alignment system shown in FIG. 6A, showing the different separations between the projected laser spots for two different cases.

As noted above, the optical payload 110 may be positioned, relative to the distal target 160, such that the distal target 160 lies at the working distance of the optical payload 110, by observing the spatial separation between the laser spots 402, 407, and identifying the spatial offset that corresponds to the minimum spot-to-spot separation. This embodiment is demonstrated in FIG. 7A, which shows the identification of the focal distance (working distance) of the optical payload as the correct spatial offset between the optical payload 110 and the distal target 160 that corresponds to the minimum distance between the laser dots 402, 407. FIG. 7B shows the spot pattern and spatial separation when the optical payload 110 is correctly positioned such that the distal target 160 lies at the working distance (left), and at an incorrect distance (right). Once again referring to FIG. 6A, it is noted that in embodiments in which alignment lasers are positioned in close proximity to the structured light detection cameras 230, 235 and with approximately the same angle as the nearest respective camera, a user may detect when the line of sight of the cameras to the distal target is being blocked by viewing the laser spots. The obstruction of the line of sight may be detected in this manner since an obstruction causing a blocked laser beam 401 and/or 406 also indicates that the respective camera 230 and/or 235 is also being blocked by the same obstruction with high likelihood.

In one example implementation, an additional alignment laser may be integrated with the optical payload 110 to generate a laser stripe 412 on the distal target 160 that is perpendicular to the alignment plane (see stripe 430 in FIG. 7B), such that when the laser spots 402, 407 lie on the laser stripe, an additional indication is provided that the correct spatial offset has been achieved.

Figure 7C:
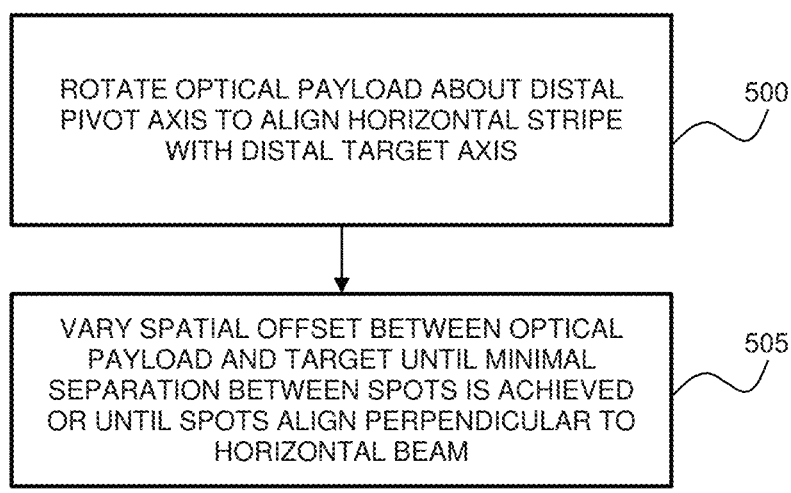
FIG. 7C is a flow chart illustrating an example method of employing the alignment lasers to align the example optical alignment system to a target in order to achieve both angular and depth alignment of the optical payload.

In one example embodiment, the optical payload 110 may be configured to include alignment lasers for generating the horizontal laser stripe 412 and the laser spots 402, 407. For example, the example embodiment illustrated in FIGS. 3A and 3B includes three alignment lasers according to this configuration. The inclusion of alignment lasers for the generation of the laser stripe 412 and the laser spots 402, 407 provides a visual indication of both rotational alignment and spatial offset alignment of the optical payload 110, as shown in FIGS. 6B and 7B. The flow chart provided in FIG. 7C illustrates a method of rotational and axial alignment of the optical payload using the visual feedback provided by the laser stripe (step 500) and the laser spots (step 505).

In yet another example implementation, an alignment laser may be integrated with the optical payload 110 and focused such that the spot size of the laser beam focuses and defocuses in a manner that is representative of the depth of field of the optical payload 110, thereby allowing the determination of the working distance based on the identification of the minimum spot size of the laser beam on the distal target 160.

Figure 8A:
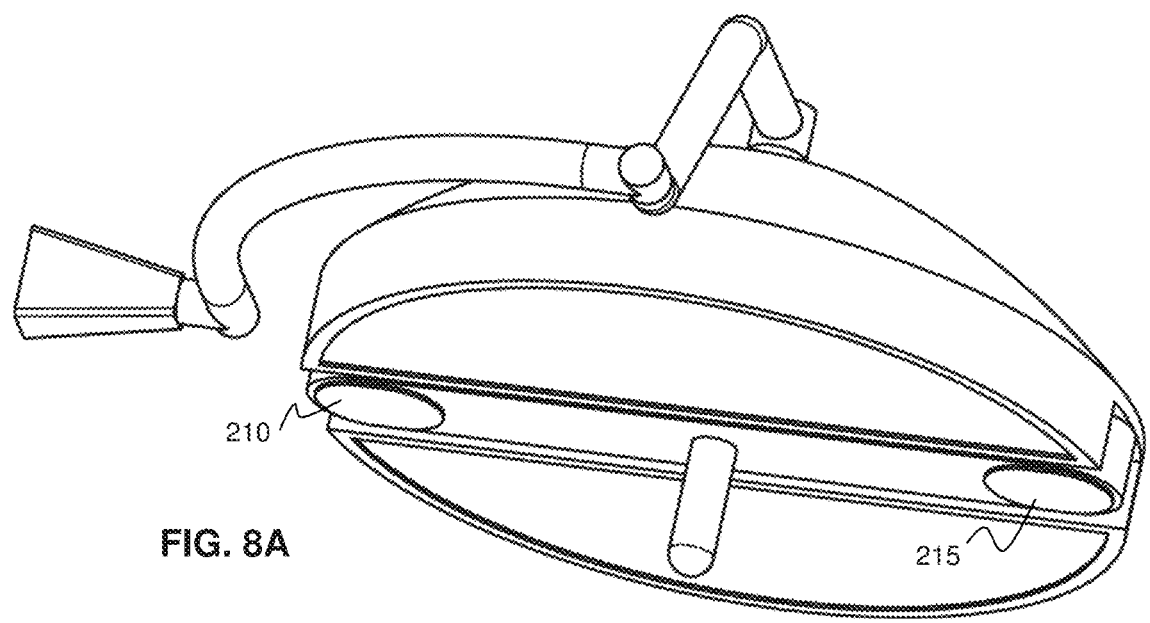
FIGS. 8A-B shows underside views of an alternative example optical alignment system including two stereoscopic optical tracking cameras.
Figure 8B:
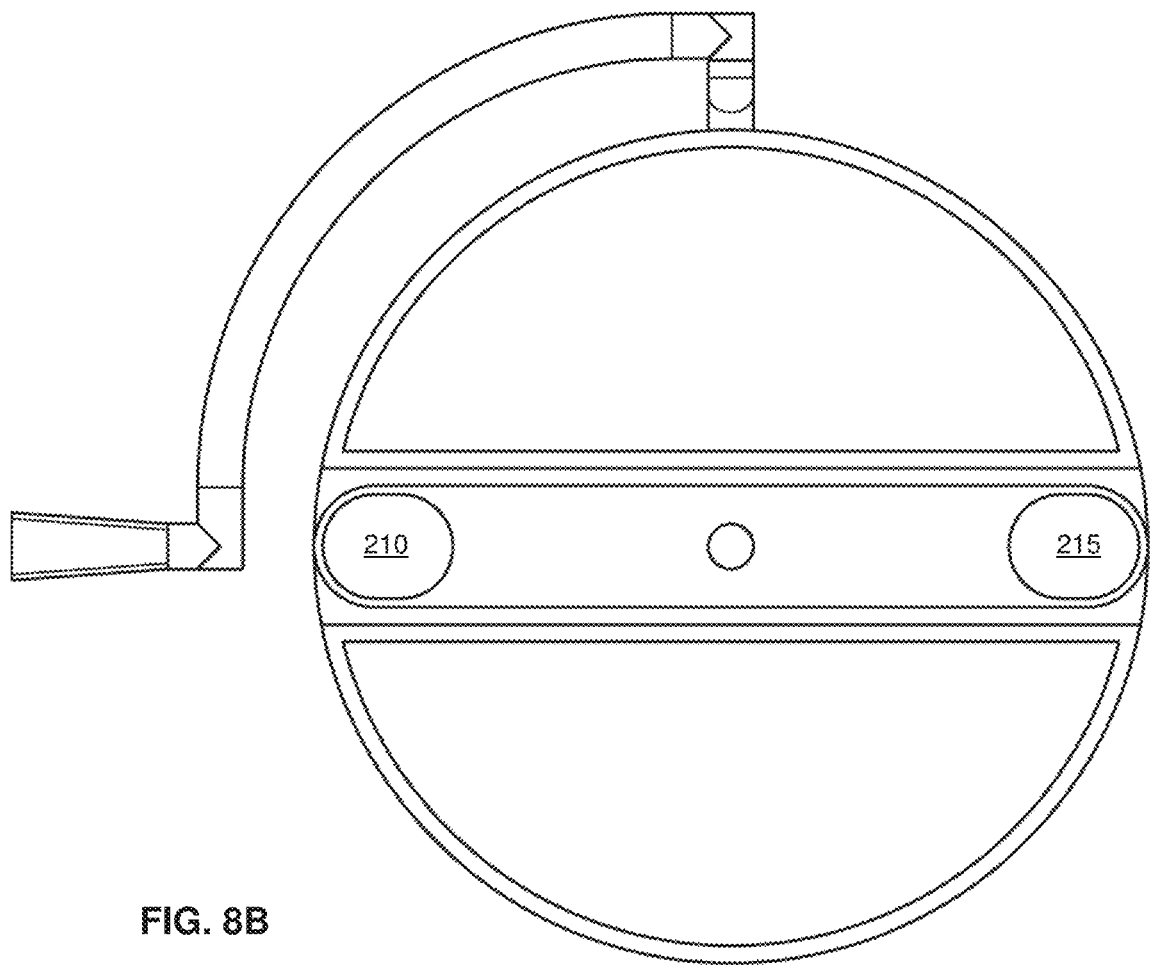
Figure 9A:
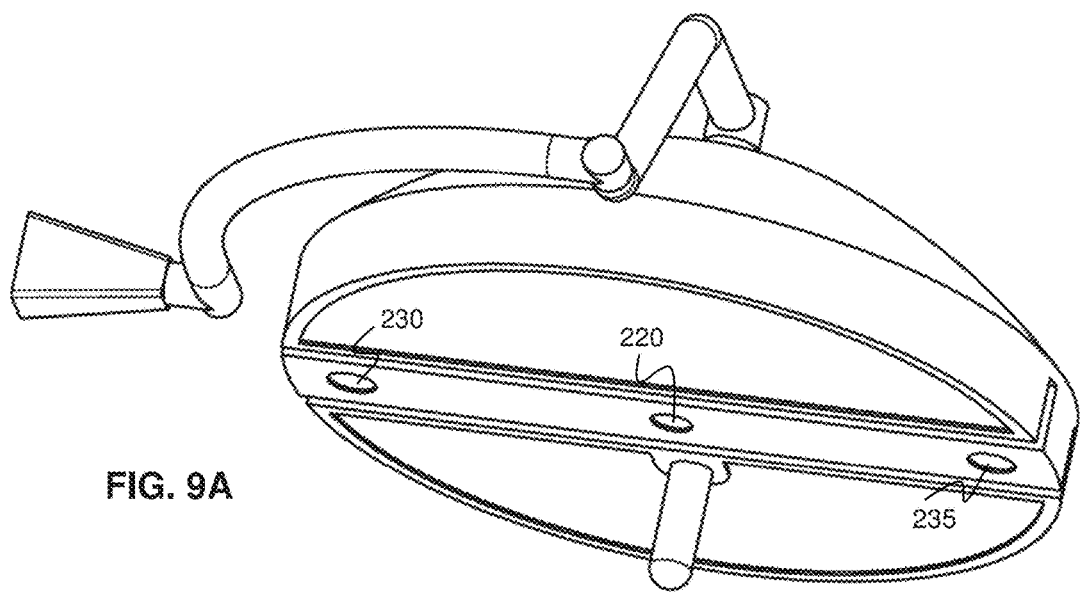
FIGS. 9A-B shows underside views of an alternative example optical alignment system including a structured light detection system consisting of two cameras and a structured light projector.
Figure 9B:
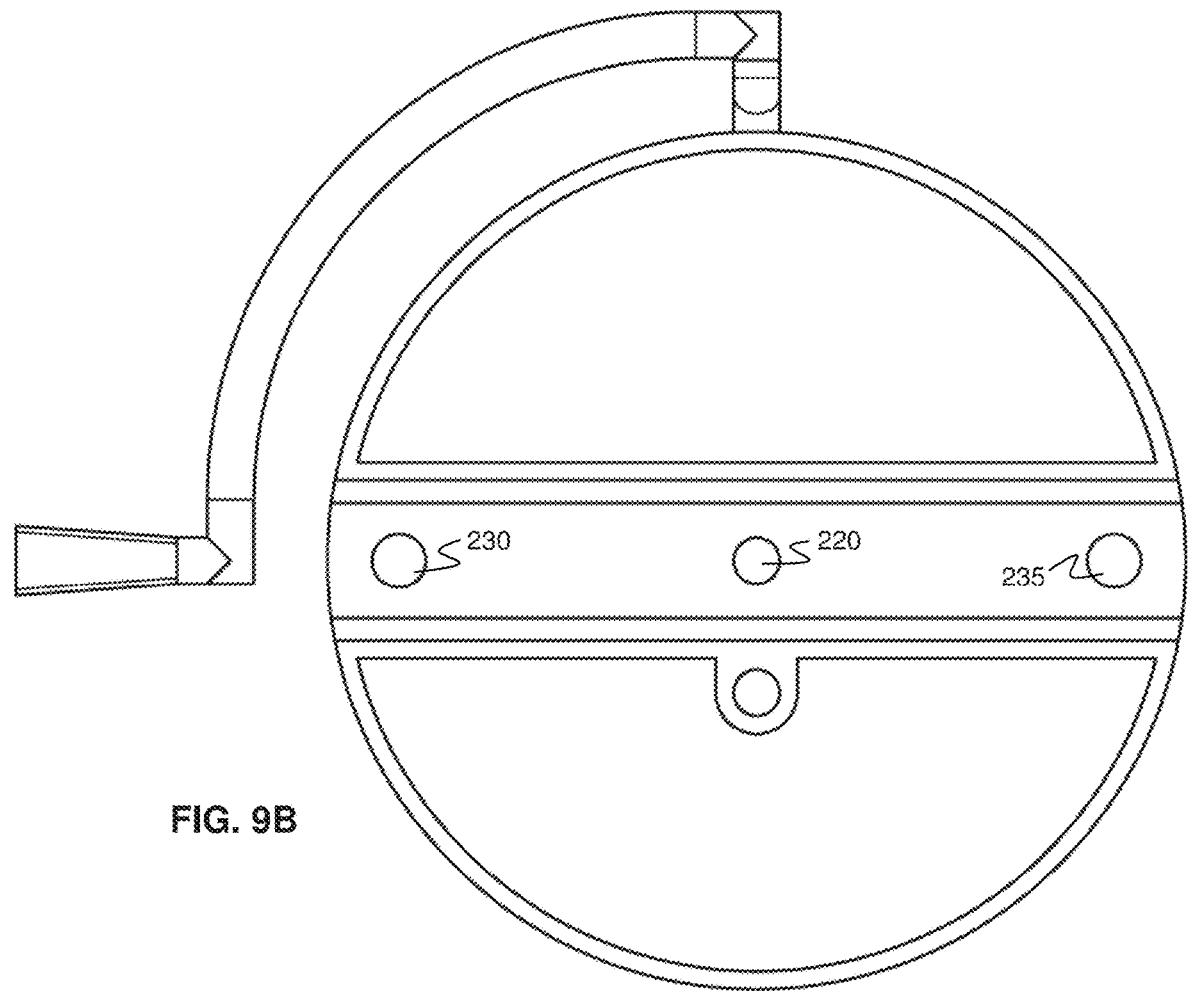
Figure 10A:
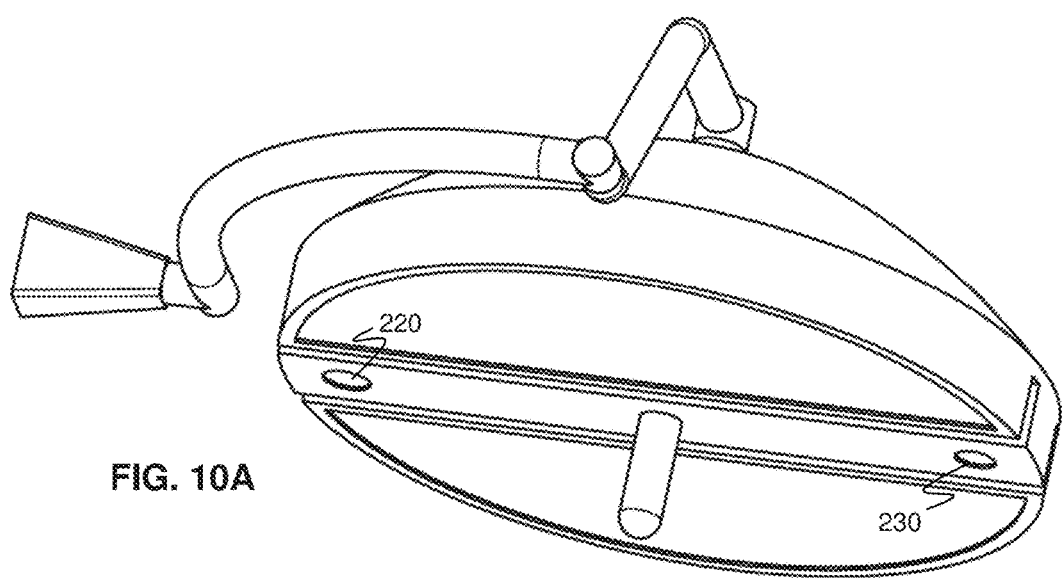
FIGS. 10A-B shows underside views of an alternative example optical alignment system including a structured light detection system consisting of a camera and a structured light projector.
Figure 10B:
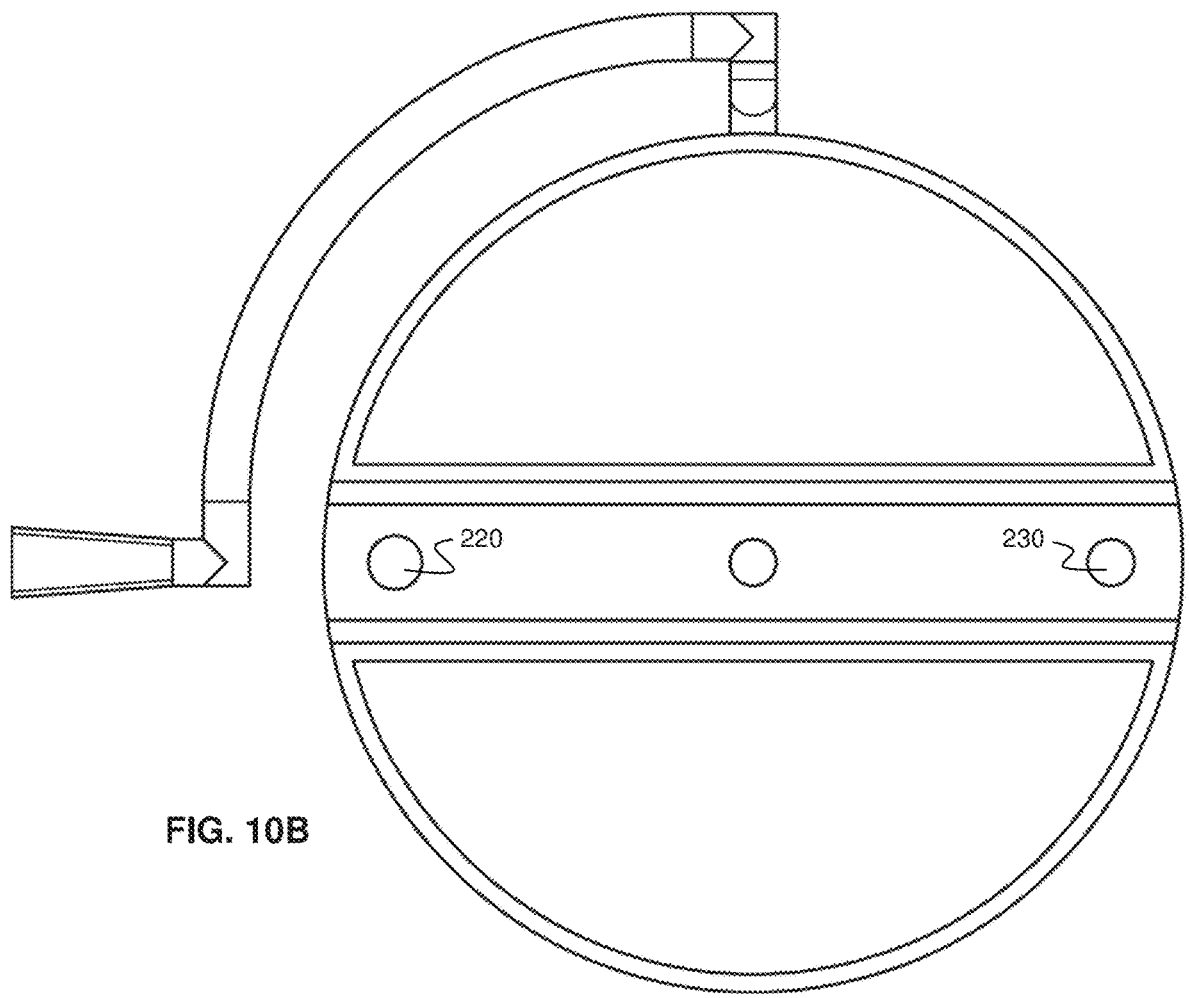
Figure 11A:
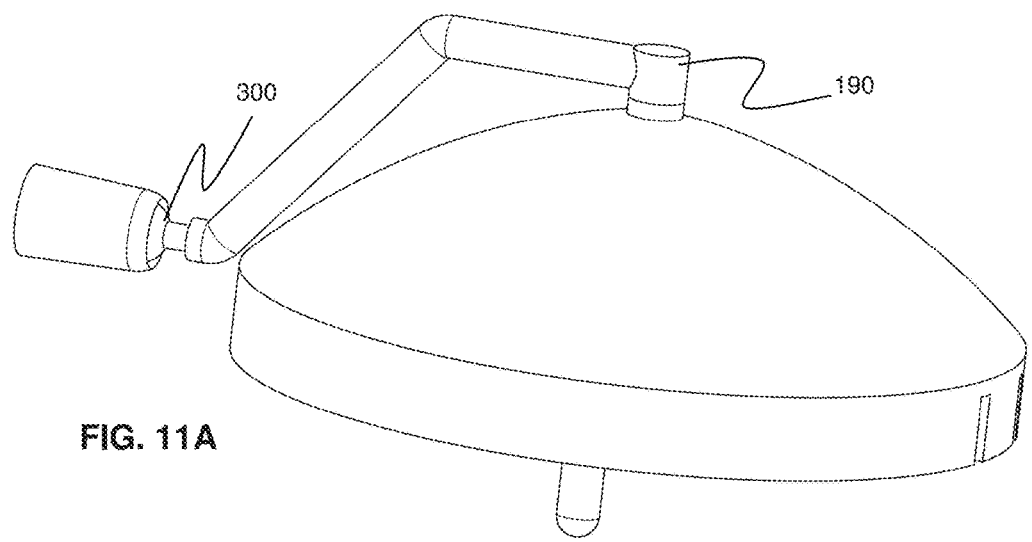
FIGS. 11A-D show top and side views of an alternative example optical alignment system in which the optical payload is supported by a two articulated segments having two associated joints, where the distal joint is a rotational pivot joint having a distal pivot axis, and the proximal joint is a ball joint.
Figure 11B:
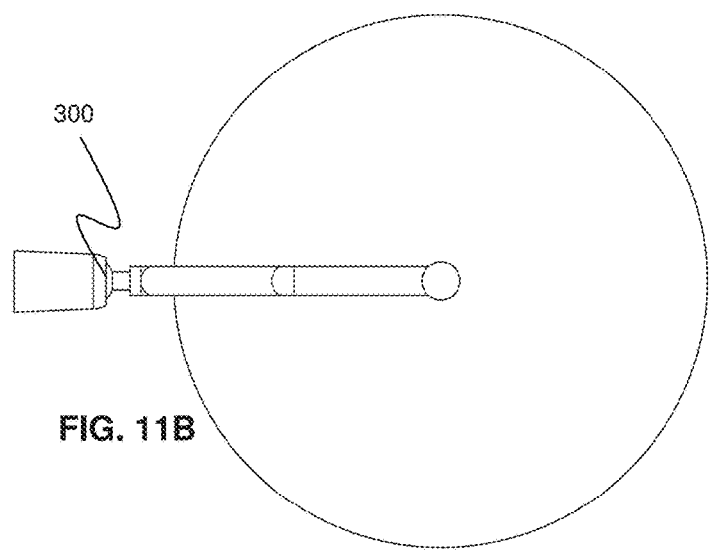
Figure 11C:
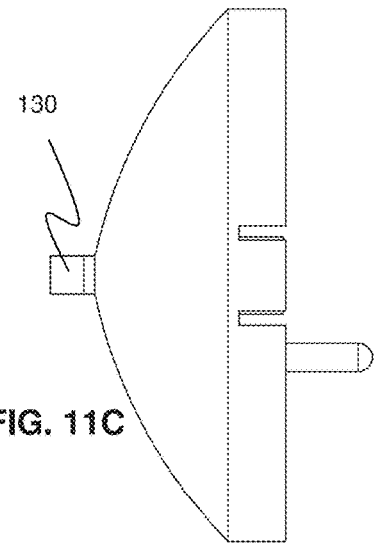
Figure 11D:
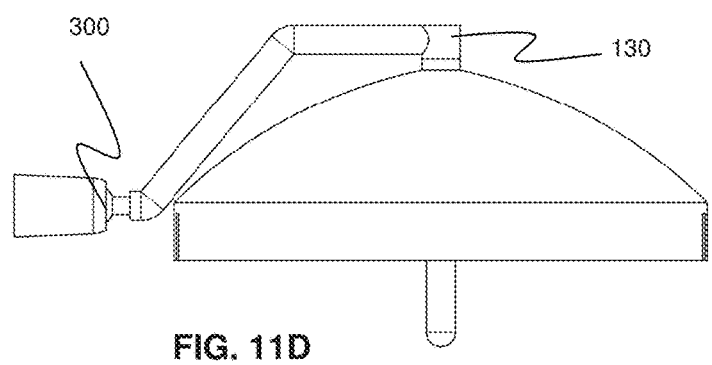

As noted above, the selection and configuration of the optical components shown in the preceding example represent but one example configuration, and this configuration is not intended to limit the scope of the present disclosure. Additional example configurations having an associated alignment plane are shown in FIGS. 8A, 8B, 9A, 9B, 10A and 10B. FIGS. 8A and 8B show an example configuration including a pair of tracking cameras 210 and 215, absent of the structured light components shown in FIGS. 3A and 3B. FIGS. 9A and 9B show an example configuration including a structured light projector 220 and a pair of structured light cameras 230 and 235, absent of the tracking cameras shown in FIGS. 3A and 3B. FIGS. 10A and 10B show an example configuration including a structured light projector 220 and a single structured light camera 230.

FIG. 11 shows an embodiment in which the two proximal pivot joints shown in previous embodiments are collapsed into a single pivot joint 300. In FIG. 11, this joint 300 is depicted as a ball joint, however in other embodiments this could also be a universal joint. The distal most pivot joint still provides rotation about the distal pivot axis while maintaining alignment to the target. The friction associated with the proximal joint will be higher than the previous embodiments in which the pivot joints are decoupled since at least one of the rotational axis associated with this pivot joint will not pass through the center of mass of the optical payload. Alternatively a locking mechanism may be used to lock the position of the ball joint once it has been positioned correctly.

With the transition from halogen bulb surgical luminaires to LED based surgical luminaires a number of new anatomically specific lighting designs may be developed. LED technologies allow much more design freedom because of their small foot print and high efficiency. Undoubtedly, some of these new designs may have a highly asymmetric output profile to meet specific procedural needs. In these situations the positioning system described here would enable that profile to be aligned to its optimal position/orientation in relation to the patient anatomy.

Another application which may benefit from the positioning system design are polarization sensitive imaging systems which may require one or more cameras utilizing polarizing filters to be aligned to a particular anatomical direction such as the axonal direction or muscle fiber direction. In these applications, the user may rotate the distal pivot axis until a maximum signal intensity is reached. This feedback may be transmitted through a user interface (video feed, or ECG type signal), LED indicators, audio signals or otherwise. While the above embodiments describe manual actuation of the positioning system it is also envisioned that the above signal optimization or the positioning in general may be robotically actuated.

The embodiments described above also have applications outside of the medical field. For example, the systems described above may be used for machine vision applications in which a polarization filter is used on both the light source and camera to reject specular reflections. Optimal rejection of specular reflection occurs when the camera polarization filter is aligned to that of the light source. However, if the light source and camera are decoupled the positioning systems described above enable alignment of the camera polarizing filter to that of the light source. In this way an entire room may be lit with light sources polarized in a single direction and the multiple camera systems may be aligned on the fly.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An optical alignment system comprising:
an optical payload having a planar distal surface;
a plurality of articulated segments having at least three pivot joints associated therewith, said plurality of articulated segments and pivot joints forming a yoke for controlling the orientation of said optical payload;
wherein said optical payload is mechanically coupled to a distal pivot joint of said pivot joints, said distal pivot joint having a distal pivot axis that is perpendicular to said planar distal surface such that:
said optical payload is axially directed at a distal target when the distal pivot axis of said distal pivot joint is directed toward the distal target; and
said optical payload is rotatable about the distal pivot axis, via the distal pivot joint, in a direction of rotation that is perpendicular to the distal pivot axis, while remaining axially directed at the distal target;
wherein said at least three pivot joints are configured such that, for any given pivot joint, a respective rotation axis associated therewith passes sufficiently close to a respective center of mass of a respective distalward portion of said optical alignment system beyond said given pivot joint, such that a position and orientation of said optical payload is maintained in the absence of external forces; and
wherein a proximal end of said optical alignment system is connectable to a positioning arm for controlling the position of the optical payload such that said distal pivot joint resides remote from the positioning arm.

2. The optical alignment system according to claim 1 wherein said optical payload comprises one or more optical components having an alignment plane associated therewith, such the alignment plane is rotatable relative to the distal target under rotation of the optical payload about the distal pivot axis, while the optical payload remains axially directed at the distal target, wherein the alignment plane includes the distal pivot axis or is parallel to the distal pivot axis.

3. The optical alignment system according to claim 2 wherein alignment plane includes a geometrical axis associated with two or more optical components.

4. The optical alignment system according to claim 3 wherein the geometrical axis is associated with a baseline separating two optical components.

5. The optical alignment system according to claim 2 wherein the alignment plane includes an alignment axis of one or more of the optical components.

6. The optical alignment system according to claim 2 wherein the alignment plane includes a polarization axis associated with one or more polarization-sensitive optical components.

7. The optical alignment system according to claim 6 wherein the one or more polarization sensitive optical components comprises a polarizing filter.

8. The optical alignment system according to claim 2 wherein said optical payload comprises a plurality of optical components, at least two of the plurality of optical components being spatial offset from the distal pivot axis and having respective optical alignment axes, respective fields of view, and respective depths of field; and
wherein said at least two optical components are oriented such that when said optical payload is (i) axially directed at the distal target at a spatial offset that is within the depth of fields of the at least two optical components and (ii) rotated about the distal pivot axis, the fields of view of the at least two optical components spatially overlap at the distal target;
thereby permitting rotational alignment of the optical alignment axes with the distal target while the optical payload remains axially directed at the distal target and while the fields of view remain spatially overlapped at the distal target.

9. The optical alignment system according to claim 8 wherein the alignment plane includes the optical alignment axes of said at least two optical components, such that when said optical payload is (i) axially directed at the distal target and (ii) rotated about the distal pivot axis, the alignment plane rotates relative to the distal target while the optical payload remains axially directed at the distal target and the fields of view remain spatially overlapped at the distal target.

10. The optical alignment system according to claim 9 wherein the alignment plane includes the distal pivot axis.

11. The optical alignment system according to claim 2 wherein said optical payload is configured to illuminate the distal target with reference beams that provide:
a visual indication of the axial offset of said optical payload from the distal target relative to the working distance; and
a visual indication of the rotational alignment of the optical payload relative to the distal target.

12. The optical alignment system according to claim 11 wherein said optical payload further comprises:

a first laser source configured to direct a first laser beam, from a first source location on said optical payload, such that the first laser beam, when unobstructed, passes through a first alignment location, wherein the first alignment location is spatially offset, in a first direction that is perpendicular to the alignment plane, from a point on the distal pivot axis that corresponds to the working distance of said optical payload;

a second laser source configured to direct a second laser beam, from a second source location on said optical payload, such that the second laser beam, when unobstructed, passes through a second alignment location, wherein the second alignment location is spatially offset, in a second direction that is perpendicular to the alignment plane, from the point on the distal pivot axis that corresponds to the working distance of said optical payload, and wherein said first direction is opposite to said second direction, such that the first alignment location and the second alignment location are on opposite sides of the alignment plane; and a third laser source configured to project a transverse alignment beam within the alignment plane;

wherein the alignment plane is a first alignment plane, and wherein the first source location and the second source location are on opposite sides of a second alignment plane that is perpendicular to the alignment plane and contains the distal pivot axis, such that the first laser beam and the second laser beam are both inwardly directed towards the first alignment location and the second alignment location, respectively;

wherein the transverse alignment beam provides the visual indication of the rotational alignment of said optical payload relative to the distal target; and wherein the first laser beam and the second laser beam produce visible reference marks on the distal target, such that the visible reference marks only intersect the second alignment plane when the distal target is located at the working distance of said optical payload, thereby providing the visual indication of the axial alignment of said optical payload relative to the working distance.

13. The optical alignment system according to claim 12 wherein the transverse alignment beam is a first transverse alignment beam, the system further comprising:

a fourth laser source configured to project a second transverse alignment beam within the second alignment plane, such that the visible reference marks only intersect the second transverse alignment beam when the distal target is located at the working distance of said optical payload.

14. The optical alignment system according to claim 2 wherein a stiffness of said distal pivot joint relative to stiffnesses of the remainder of the at least three pivot joints is configured such that, after having established an initial position and orientation of said optical payload relative to an external reference frame, a rotational orientation of said optical payload relative to the distal pivot axis is variable without causing actuation of the remainder of the at least three pivot joints.

15. The optical alignment system according to claim 2 wherein at least two of said at least three pivot joints have perpendicular pivot axes.

16. The optical alignment system according to claim 2 wherein said one or more optical components comprise a stereo camera pair.

17. The optical alignment system according to claim 16 wherein said one or more optical components further comprises a structured light projector.

18. The optical alignment system according to claim 2 wherein said one or more optical components comprise at least one camera and a structured light projector.

19. A method of aligning an optical payload with a distal target, the method comprising:
  providing an optical alignment system according to claim 2;
  actuating the at least three pivot joints such that the optical payload is axially directed at the distal target; and
  while axially directing the optical payload at the distal target, rotating the optical payload relative to the distal pivot axis such that the alignment plane is rotationally aligned with the distal target.

20. The method according to claim 19 wherein the distal target has a distal target axis associated therewith, and wherein the optical payload is rotated about the distal pivot axis such that the alignment plane includes the distal target axis.

* * * * *